United States Patent [19]
Bachar et al.

[11] Patent Number: 5,848,984
[45] Date of Patent: Dec. 15, 1998

[54] APPARATUS FOR RELIEVING BACK PAIN

[75] Inventors: Avraham Bachar, 23 Brande Street, Petach Tikva, Israel, 49600; Raanan Volk, Ramat Gan, Israel

[73] Assignee: Avraham Bachar, Petach Tivka, Israel

[21] Appl. No.: 709,780

[22] Filed: Sep. 9, 1996

Related U.S. Application Data

[63] Continuation of Ser. No. 675,164, Jul. 3, 1996, abandoned.

[30] Foreign Application Priority Data

Jul. 5, 1995 [IL] Israel ......................................... 114473

[51] Int. Cl.⁶ ......................................................... A61F 5/00
[52] U.S. Cl. .............................................. 602/32; 602/36
[58] Field of Search ................................ 602/19, 32–36, 602/38, 40; 601/24, 26, 33, 97, 98, 100, 101; 606/240, 241; 297/284.7, 464, 465

[56] References Cited

U.S. PATENT DOCUMENTS

| | | |
|---|---|---|
| 1,650,650 | 11/1927 | Pieper . |
| 1,722,205 | 7/1929 | Freund . |
| 2,667,913 | 2/1954 | Dustin . |
| 2,886,031 | 5/1959 | Robbins . |
| 3,029,810 | 4/1962 | Martin . |
| 3,167,068 | 1/1965 | Carr ......................................... 602/32 |
| 3,675,646 | 7/1972 | Corcoran . |
| 4,487,201 | 12/1984 | Ciambarella et al. . |
| 4,565,409 | 1/1986 | Hollonbeck et al. . |
| 4,715,362 | 12/1987 | Scott . |
| 4,860,733 | 8/1989 | Parker, Jr. . |
| 4,881,528 | 11/1989 | Scott ......................................... 602/32 |
| 4,996,978 | 3/1991 | Gingras . |
| 5,033,459 | 7/1991 | Burton . |
| 5,171,317 | 12/1992 | Concoran ................................ 606/241 |
| 5,176,706 | 1/1993 | Lee . |
| 5,195,949 | 3/1993 | Burton et al. . |
| 5,224,924 | 7/1993 | Urso . |
| 5,336,965 | 8/1994 | Sessini ............................. 297/284.7 X |
| 5,437,609 | 8/1995 | Leonard et al. ...................... 601/98 X |
| 5,460,427 | 10/1995 | Serber ............................. 297/284.7 X |

FOREIGN PATENT DOCUMENTS 2363390 6/1975 Germany ................................ 606/241

*Primary Examiner*—Richard J. Apley
*Assistant Examiner*—Denise Pothier
*Attorney, Agent, or Firm*—Darby & Darby

[57] ABSTRACT

A seat supportable device for relieving lower back pressure is provided. The device includes a seat portion arranged to be supported on a seat and to be sat upon by a user, a rib cage engagement portion arranged to removably engage the rib cage of the user when he is sitting on the seat portion and user controlled tensioning apparatus for selectably applying tension between the rib cage engagement portion and the seat portion, thereby to relieve lower back pressure on the user.

6 Claims, 25 Drawing Sheets

APPARATUS FOR RELIEVING BACK PAIN

This application is a continuation of U.S. patent application Ser. No. 08/675,164, filed Jul. 3, 1996, now abandoned.

FIELD OF THE INVENTION

The present invention relates to apparatus for relieving lower back pressure.

BACKGROUND OF THE INVENTION

Various devices are known for relieving lower back pressure. These include devices for transferring stress to the rib cage of a person. The state of the art as reflected in the U.S. Patent literature is represented by the following U.S. Pat. Nos. 5,224,924; 5,195,949; 4,996,978; 4,715,362; 4,565,409; 3,029,810; 2,886,031; 2,667,913; 1,722,205; and 1,650,650.

SUMMARY OF THE INVENTION

The present invention seeks to provide improved apparatus for relieving lower back pressure.

There is thus provided in accordance with a preferred embodiment of the present invention a seat supportable device for relieving lower back pressure which includes a seat portion arranged to be supported on a seat and to be sat upon by a user, a rib cage engagement portion arranged to removably engage the rib cage of the user when he is sitting on the seat portion and user controlled tensioning apparatus for selectably applying tension between the rib cage engagement portion and the seat portion, thereby to relieve lower back pressure on the user.

The user controlled apparatus may include user arm engageable apparatus or alternatively powered apparatus, such as electrically powered, pneumatically powered or hydraulically powered apparatus.

The rib cage engagement portion may be in the form of a strap which surrounds the chest of a user, apparatus which engages the arms or shoulders of the user or any other apparatus which can be used for applying an upward vertical force to the upper portion of the spine.

In accordance with a preferred embodiment of the invention, the user controlled tensioning apparatus includes a lever arm engageable by a user's arm when sitting on the seat portion and when his rib cage is engaged by the rib cage engagement portion and which is operative when pivoted to apply a user-controlled amount of tension between the seat portion and the rib cage engagement portion.

Preferably, the user controlled tensioning apparatus includes a spring or other resilient element disposed between the lever arm and rib cage engagement assembly.

In accordance with a preferred embodiment of the present invention, the user controlled tension apparatus includes a ratchet mechanism allowing the tensioning apparatus to be operated by successive reciprocal movements of the lever arm.

Preferably, the user controlled tension apparatus includes a frame assembly including a fixed frame element, at least one eccentrically mounted cam element rotatably mounted with respect to the fixed frame element and at least one cam following frame element which is vertically displayed relative to the fixed frame element by rotation of the at least one eccentrically mounted cam element, the rib cage engagement assembly being mounted onto the at least one cam following frame element.

Additionally in accordance with a preferred embodiment of the present invention the user controlled tensioning apparatus preferably includes a retaining assembly, for selectably retaining the tensioning apparatus in a selected tension-applying state even in the absence of continued user engagement with the lever arm.

In accordance with another preferred embodiment of the present invention, the user controlled tensioning apparatus includes a motor.

There is also provided in accordance with a preferred embodiment of the present invention a method for relieving lower back pain including:

a) sitting on a seat portion, supported on a seat;

b) engaging a rib cage engagement portion with one's rib cage; and c) employing user controlled tensioning apparatus for selectably applying tension between the rib cage engagement portion and the seat portion, thereby to relieve lower back pressure.

In accordance with another preferred embodiment of the present invention the seat portion includes a bottom portion connected to a back portion.

In accordance with another preferred embodiment of the present invention, the bottom portion includes a raised element connected at one end to a generally flat element and inflatable means interposed between the raised element and the flat element.

In accordance with another preferred embodiment of the present invention, the user controlled tensioning apparatus includes means for altering the position of the bottom portion relative to the back portion thereby applying tension.

In accordance with another preferred embodiment of the present invention a resilient element is disposed intermediate the bottom and back portions.

In accordance with another preferred embodiment of the present invention, the rib cage forms part of the back portion.

There is also provided, in accordance with a preferred embodiment of the present invention, apparatus for relieving lower back pressure of a user which includes a seat portion arranged to be supported on a seat and a rib cage engagement assembly arranged to removably engage the rib cage of said user. The seat portion includes a bottom portion and a back portion. The rib cage engagement assembly is connected to the back portion.

In accordance with another preferred embodiment of the present invention, the back portion is movable with respect to the bottom portion about an axis formed by a connection element therebetween.

In accordance with another preferred embodiment of the present invention, the apparatus further includes means for removably mounting the rib cage to the back portion when the user is sitting on the bottom portion. The rib cage is engaged to the user and to the back portion. Movement of the back portion relative to the bottom portion provides tension between the back portion and the rib cage assembly, thereby to relieve lower back pressure.

In accordance with another preferred embodiment of the present invention, the apparatus further includes means for moving the rib cage relative to the back portion when the user is sitting thereon and user controlled tensioning apparatus for selectably applying tension between the rib cage engagement assembly and the bottom portion.

In accordance with another preferred embodiment of the present invention, the controlled tensioning apparatus includes upper and lower support members attached to the back portion, a lead screw freely supported at each end by the upper and lower support members, a nut threaded onto the lead screw and an operating device for rotating the screw. The nut is attached to the rib cage engagement assembly.

In accordance with another preferred embodiment of the present invention, the controlled tensioning apparatus includes upper and lower support members attached to the back portion, a third support member attached to the rib cage engagement assembly, a tensioning cable coupled at one end thereof to the upper support member and an operating device for applying tension to the tensioning device.

In accordance with another preferred embodiment of the present invention, the controlled tensioning apparatus includes means for altering the position of the rib cage assembly relative to the bottom portion thereby applying tension.

In accordance with another preferred embodiment of the present invention, the altering means includes raising means interposed between the bottom portion and the rib cage assembly.

In accordance with another preferred embodiment of the present invention, the raising means includes inflatable means connected to the rib cage assembly.

In accordance with another preferred embodiment of the present invention, the raising means includes a lead screw device attached to a motor at one end thereof and freely rotatable at its other, a nut threaded onto the lead screw and an operating device for rotating said screw. The nut is attached to the rib cage engagement assembly.

Additionally, in accordance with another preferred embodiment of the present invention, there is provided apparatus for relieving lower back pressure which includes a seat portion arranged to be supported on a seat and a rib cage engagement assembly arranged to removably engage the rib cage of the user and the seat portion. In one embodiment the seat portion forms part of the seat itself.

In accordance with another preferred embodiment of the present invention the rib cage engagement assembly includes an extendable portion integrally connected thereto, wherein the engagement of the extendable portion with the seat portion applies tension to the rib cage engagement assembly. In one preferred embodiment the extendable element is a resilient element.

In accordance with another preferred embodiment of the present invention, the seat portion includes an element integrally connected thereto. The engagement of the element and the seat portion applies tension to the rib cage engagement assembly to relieve lower back pressure of said user.

Finally, there is also provided a method for relieving lower back pain including:

a) sitting on a seat portion, supported on a seat; and b) engaging a rib cage engagement portion with one's rib cage and the seat portion to apply tension between the rib cage engagement portion and the seat portion, thereby to relieve lower back pressure.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1A:
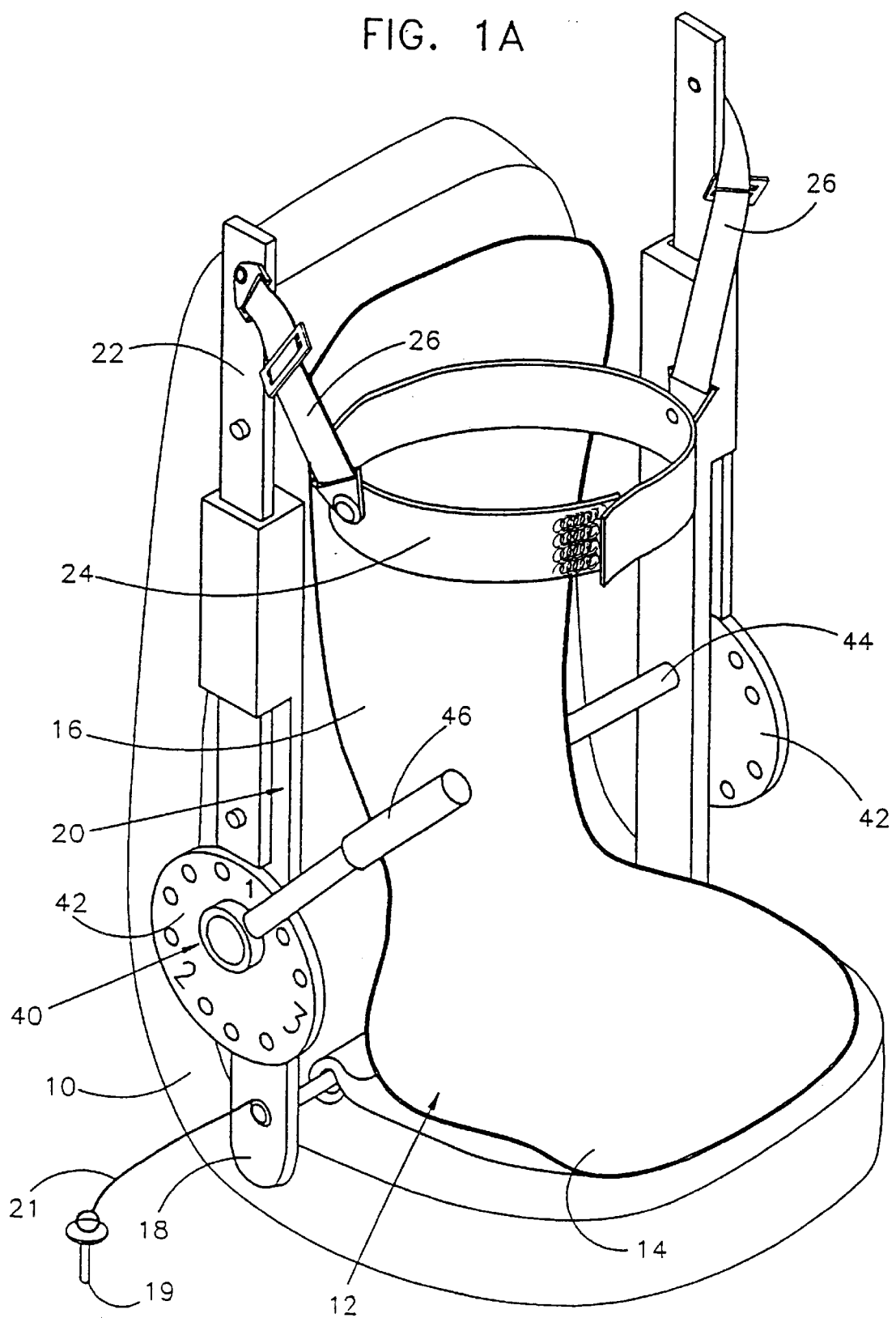
FIGS. 1A and 1B are simplified pictorial illustrations of a chair mounted device for relieving lower back pressure constructed and operative in accordance with a preferred embodiment of the present invention in respective first and second operative orientations.

Reference is now made to FIGS. 1A, 1B, 2A and 2B, which illustrate apparatus for relieving lower back pressure constructed and operative in accordance with a preferred embodiment of the present invention.

The apparatus for relieving lower back pressure constructed and operative in accordance with a preferred embodiment of the present invention is arranged to be mounted onto an ordinary chair 10 or other seat, such as an automobile seat. A preferably flexible seat supported element 12 is located on a seat and preferably includes a bottom portion 14 and a back portion 16, preferably integrally formed therewith. The bottom portion 14 and the back portion 16 are preferably ergonometrically designed.

The bottom portion 14 is fixedly mounted onto a fixed bottom portion 18 of a generally vertically extending frame assembly 20, which also includes an upper vertically sliding portion 22. A rib cage engaging belt 24 is supported onto the vertically sliding portion 22 by means of adjustable resilient straps 26.

Preferably the bottom portion 18 and the upper portion 22 are arranged in mutually telescopic arrangement.

In accordance with a preferred embodiment of the present invention a lever arm driven frame extension assembly 40 is provided for selectably raising the upper portion 22 and thus, via resilient straps 26, raising the rib cage of a user relative to the lower part of his body. The assembly 40 preferably comprises a pair of eccentrically mounted cams 42 which are fixed to an axle 44 rotatably mounted in the bottom portion 18 of frame assembly 20. Axle 44 is preferably bifurcated to enable frame 20 to be of expandable width so as to accommodate seats and users of differing widths.

Figure 3A:
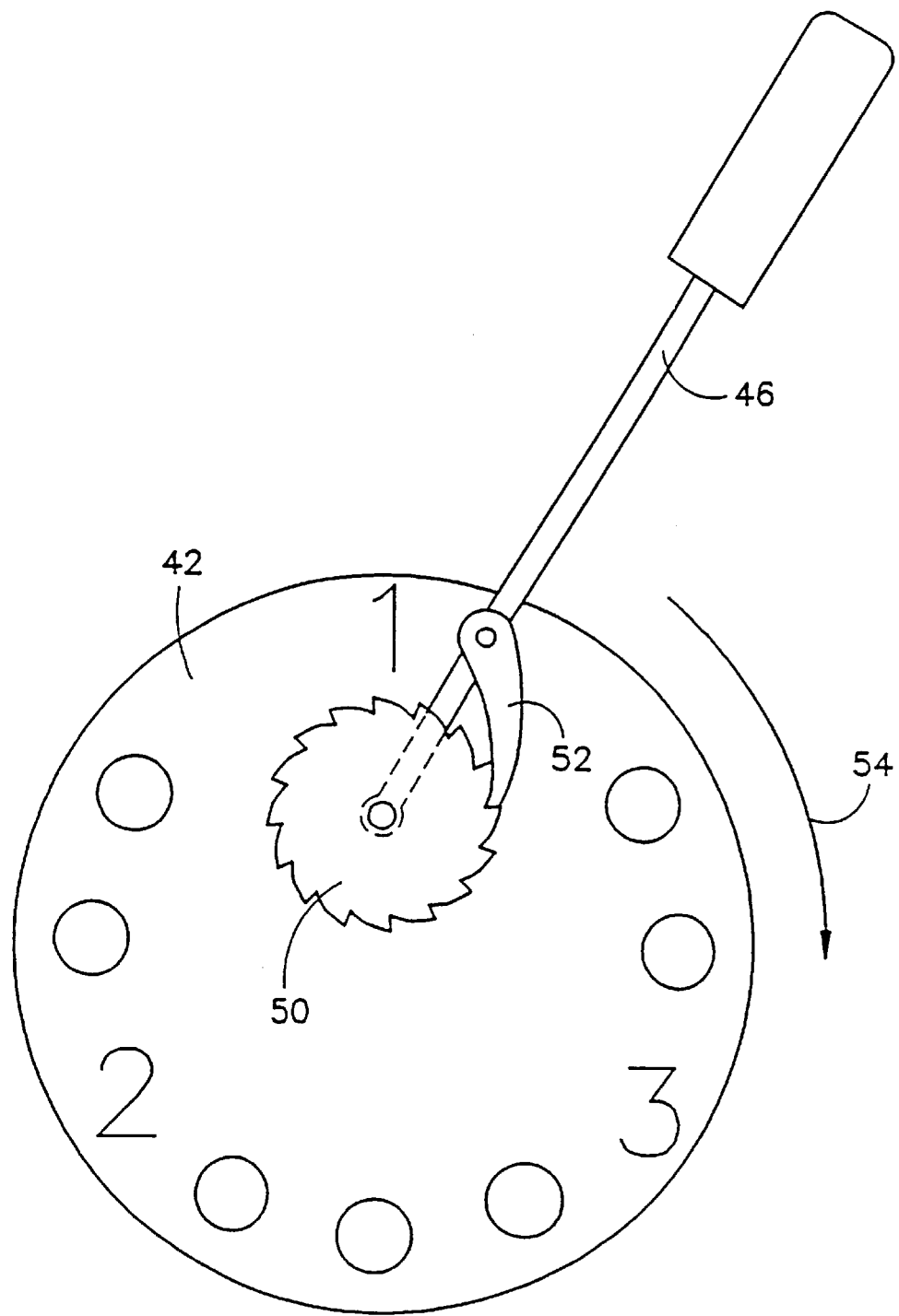
FIGS. 3A, 3B and 3C are illustrations of a typical ratchet assembly preferably employed in the apparatus of FIGS. 1A–2B.
Figure 3B:
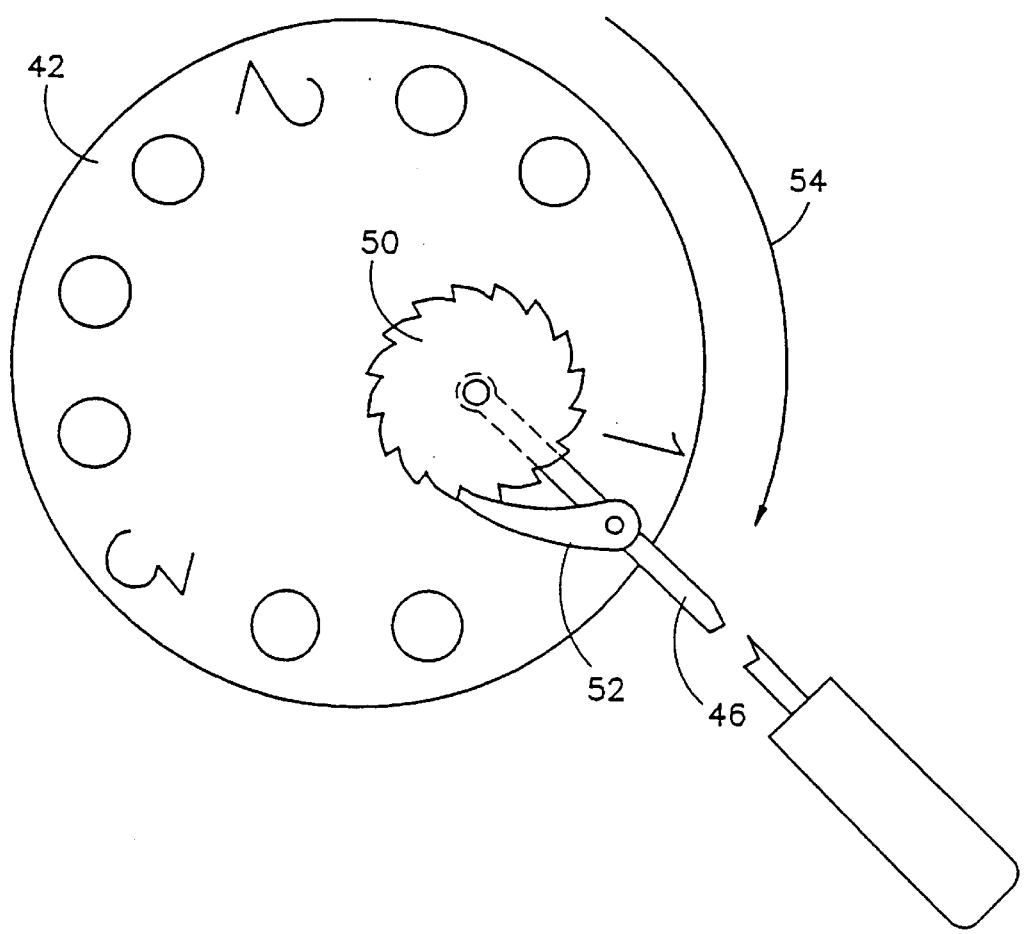
Figure 3C:
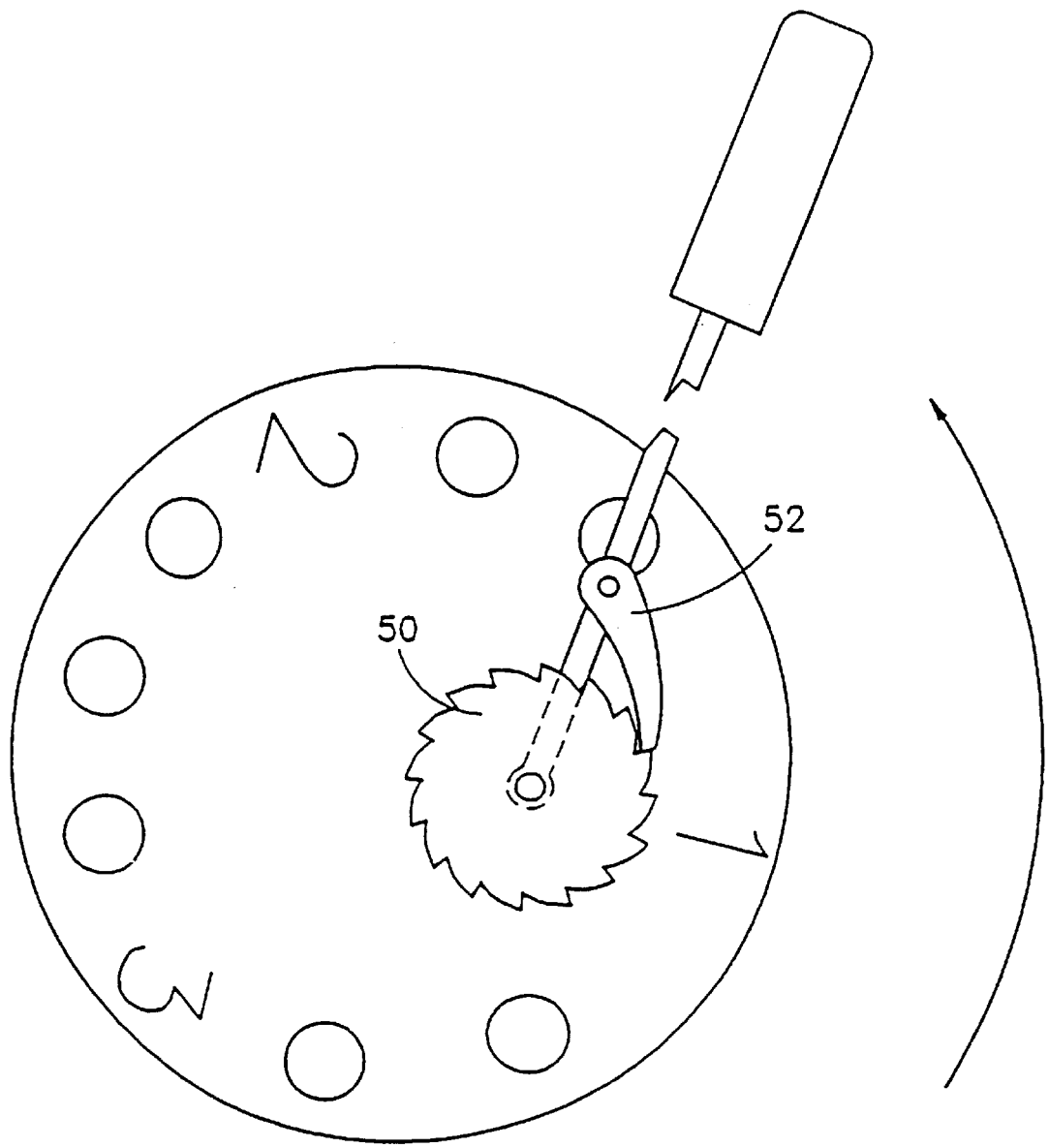

A lever arm 46 is operative to rotate cams 42 and axle 44 via a ratchet assembly illustrated in FIGS. 3A–3C so as to selectably raise or lower upper portion 22 relative to bottom portion 18.

Referring now to FIGS. 3A–3C it is seen that a toothed wheel 50 is fixedly mounted onto cam 42 and is centered about the axis of axle 44. Lever arm 46 is pivotably mounted about the axis of axle 44 and is provided with a pivotably mounted ratchet engagement member 52, which engages the teeth of the toothed wheel 50, such that when the lever arm is moved downward in the sense indicated by arrow 54, both the toothed wheel 50 and the cam 42 together therewith are rotated about the axis of axle 44 in the sense of arrow 54. When the lever arm 46 is raised in the direction opposite to arrow 54, engagement member 52 slides over the teeth of wheel 50.

Figure 1B:
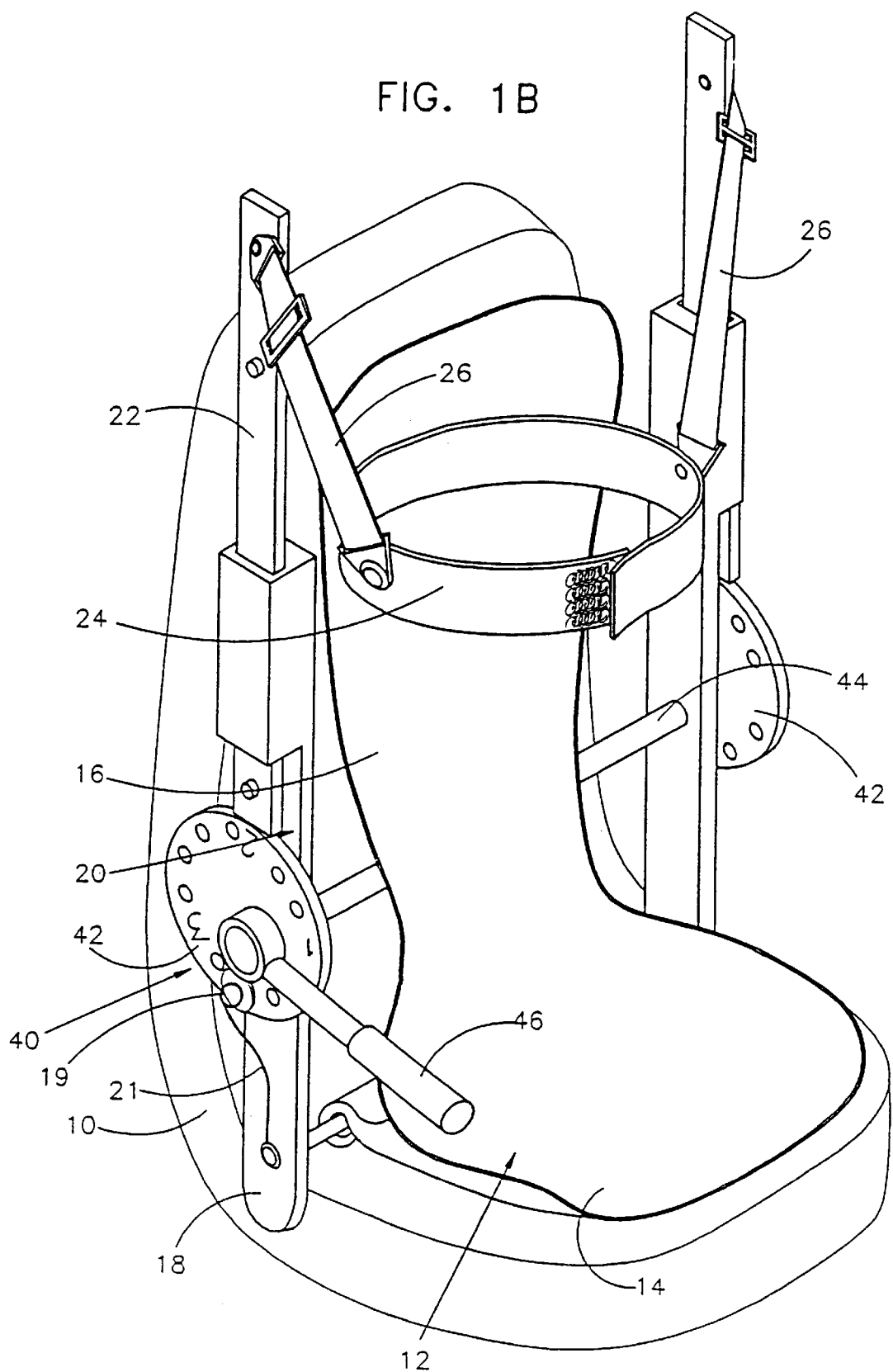

After rotating cam 42 to a desired position, cam 42 may be secured by means of a safety pin 19 which engages a hole on cam 42 and fixes cam 42 with bottom portion 18, as seen in FIG. 1B. As seen in FIGS. 1A and 1B, safety pin 19 may be attached to portion 18 with a string or chain 21. Safety pin 19 is illustrated in FIGS. 1A and 1B for engagement with the cam 42 on the side of frame 20 with lever arm 46. Alternatively, safety pin 19 may be mounted for engagement with cam 42 on the other side of frame 20.

FIG. 3A illustrates the arrangement prior to downward movement of the lever arm 46. FIG. 3B illustrates the arrangement when the lever arm 46 has been moved downward in the sense indicated by arrow 54. FIG. 3C illustrates the arrangement after the lever arm 46 has been raised by movement in a sense opposite to that indicated by arrow 54.

Figure 2A:
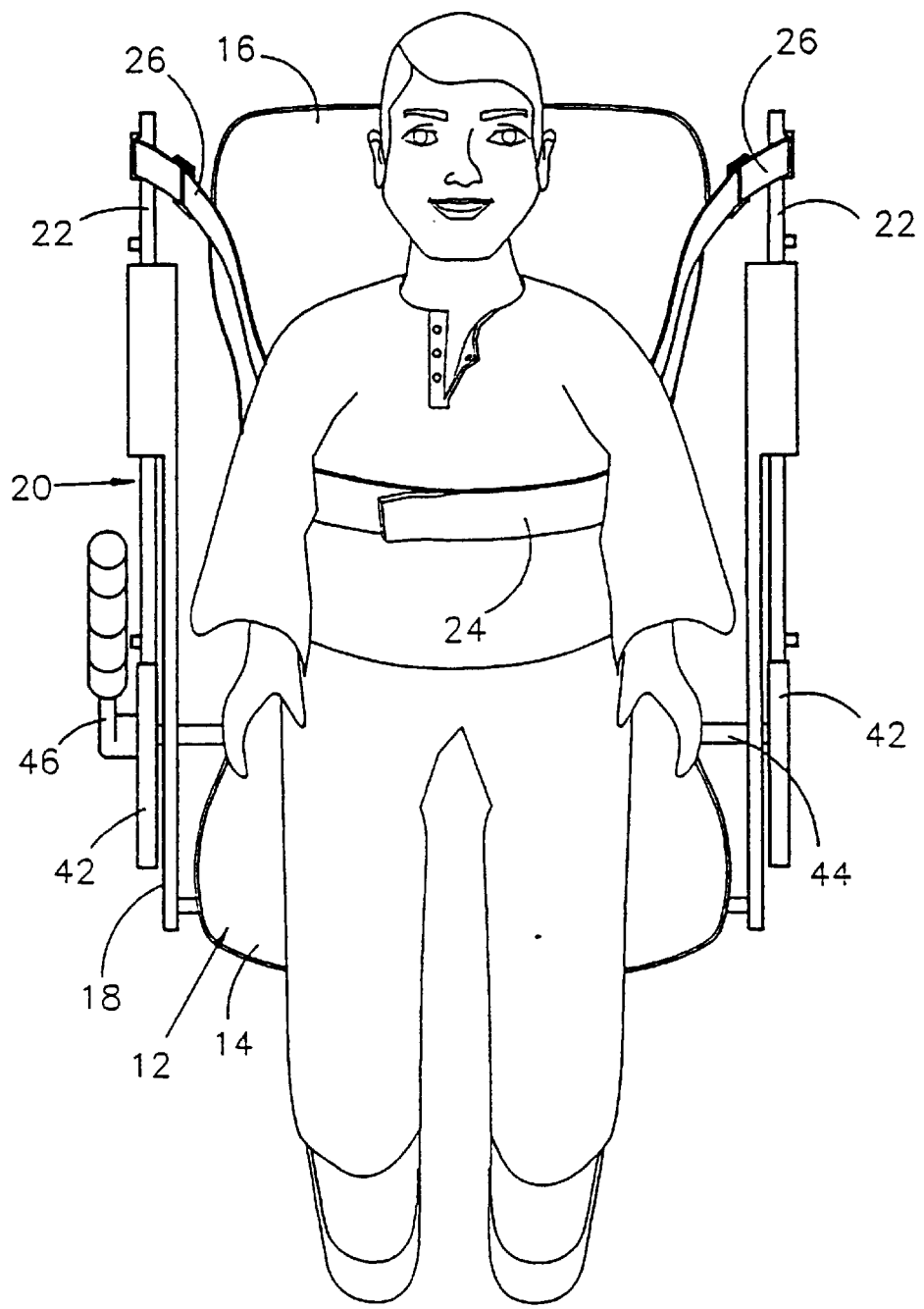
FIGS. 2A and 2B are simplified pictorial illustrations of a user employing the chair mounted device of FIGS. 1A and 1B for relieving lower back pressure in the first and second operative orientations shown respectively in FIGS. 1A and 1B.
Figure 2B:
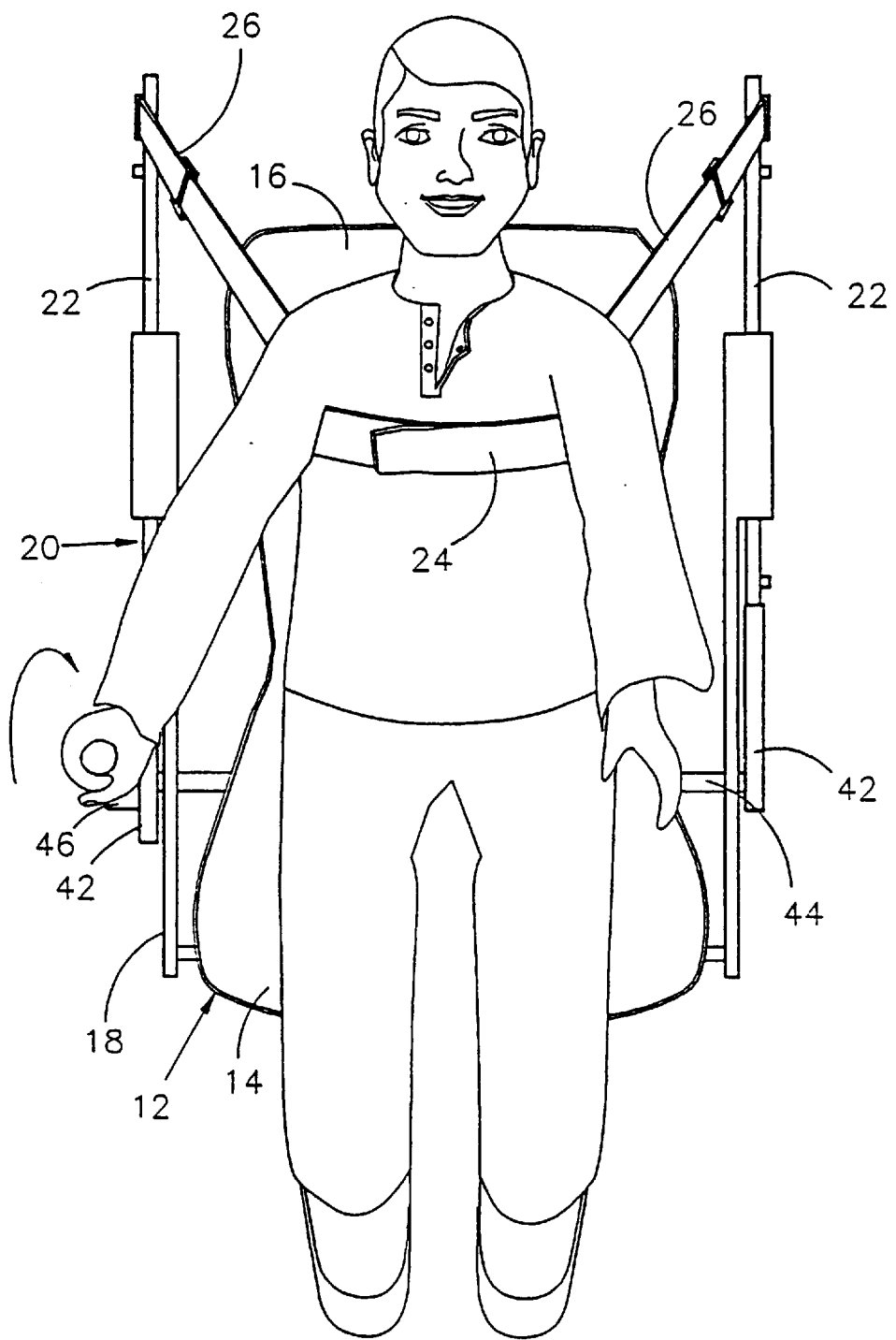

The operation of the apparatus of FIGS. 1A–3C will now be described with reference to the drawings:

Considering an initial state of operation represented by FIGS. 1A, 2A and 3A, it is seen that cams 42 are located such that the bottom of each upper portion 22 lies on a location "1" on the edge surface of a cam 42. Rotation of lever arm 46 via the ratchet assembly shown in FIGS. 3A–3C causes the cams 42 to rotate about an axis defined by axle 44, thus causing the bottom of each upper portion 22 to lie at a location "2" on the edge surface of cam 42. Since location "2" is distanced further from the axis defined by axle 44 than is located "1", the rotation of the cams 42 causes the upper portion 22 to be raised relative to the bottom portion 18.

Raising of the upper portion 22 imparts a raising force to the rib cage engaging belt 24 via resilient straps 26. It is appreciated that resilient straps 26 are employed to prevent possibly harmful over-tensioning of the user's rib cage and to absorb sudden forces which might otherwise be applied directly to the user's rib cage.

Upper portion 22 may be lowered relative to the bottom portion 18 by further rotation of cams 42 using lever arm 46.

Reference is now made to FIGS. 4A, 4B, 5A and 5B, which illustrate a chair mounted device for relieving lower back pressure constructed and operative in accordance with another preferred embodiment of the present invention in respective first and second operative orientations.

The apparatus of FIGS. 4A–5B is essentially similar to that of FIGS. 1A–3C except in that upper portion 22 and resilient straps 26 are replaced by an intermediate portion 62, which is generally vertically slidable with respect to the bottom portion 18, and an upper portion 64, which is generally vertically slidable with respect to the intermediate portion 62. Preferably the bottom portion 18 and the upper portion 64 are arranged in a mutually telescopic arrangement with respect to the intermediate portion 62, as illustrated. A pair of springs 66 are preferably arranged between the intermediate and upper portions 62 and 64 of frame assembly 20 for urging the two portions towards each other.

A rib cage engagement assembly 70 is mounted onto the upper portion 64 of frame assembly 20 by means of adjustable attachment straps 72 and includes a removable rib cage engaging strap assembly 74.

Figure 4A:
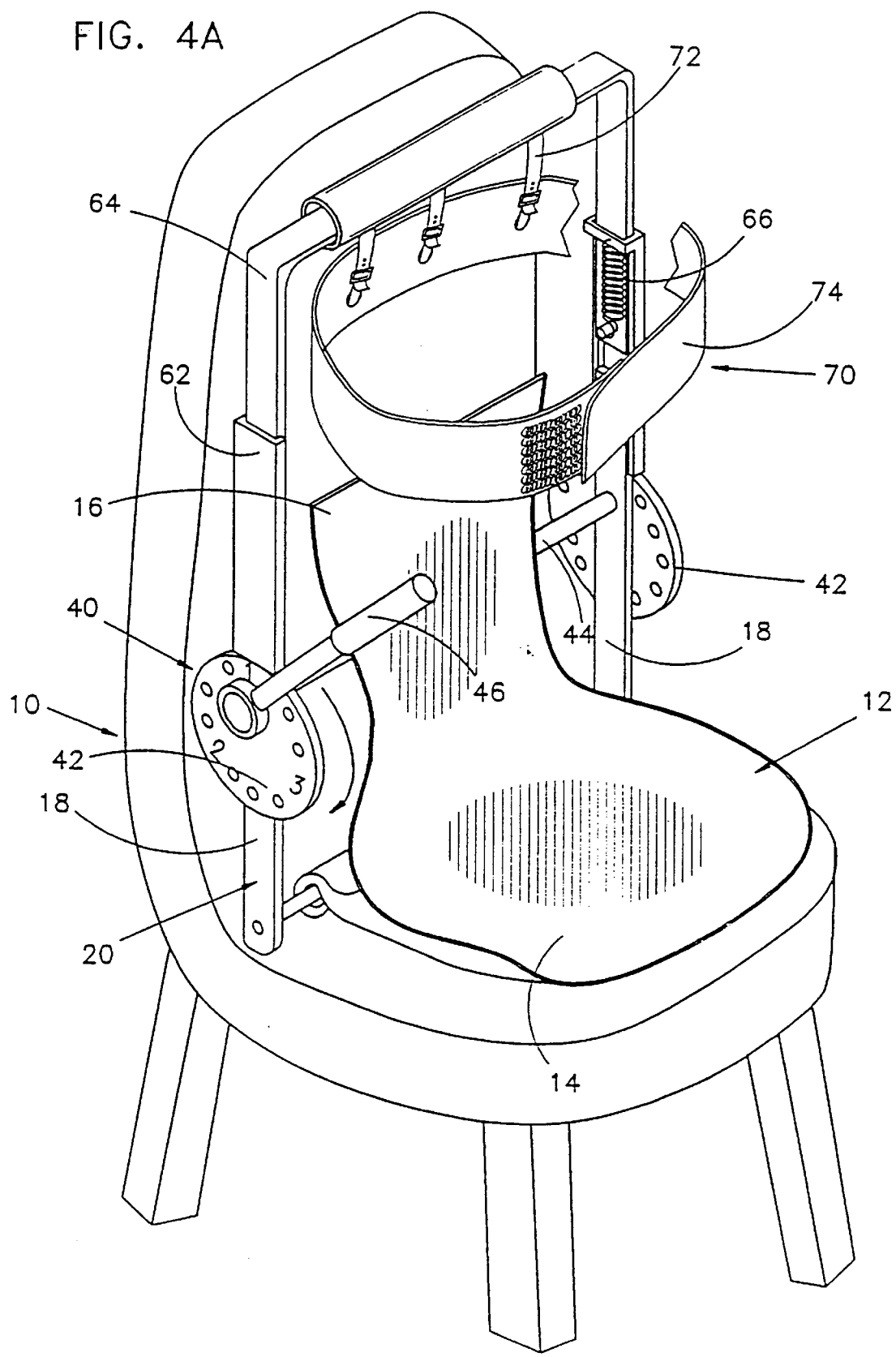
FIGS. 4A and 4B are simplified pictorial illustrations of a chair mounted device for relieving lower back pressure constructed and operative in accordance with another preferred embodiment of the present invention in respective first and second operative orientations.
Figure 4B:
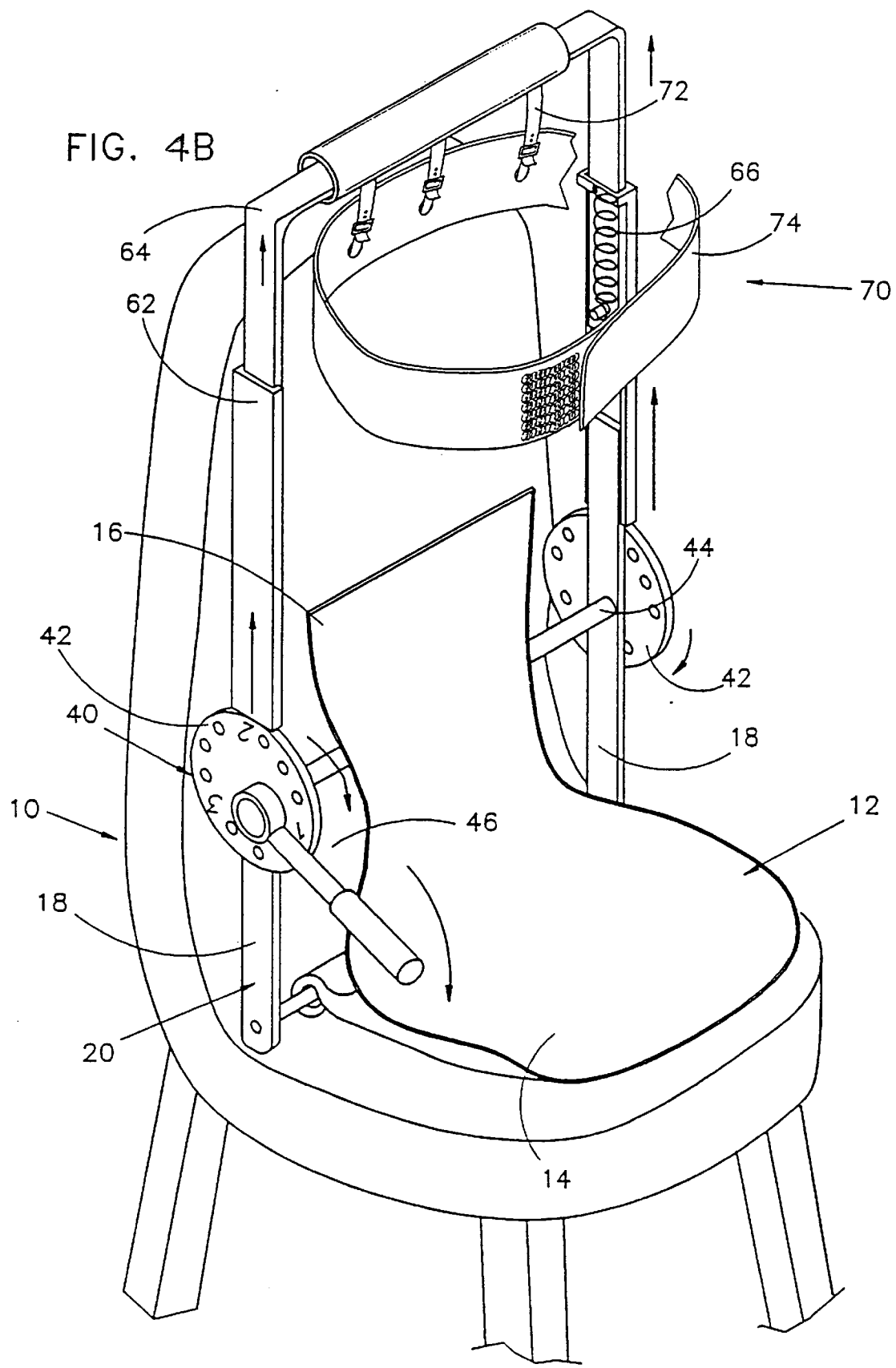
Figure 5A:
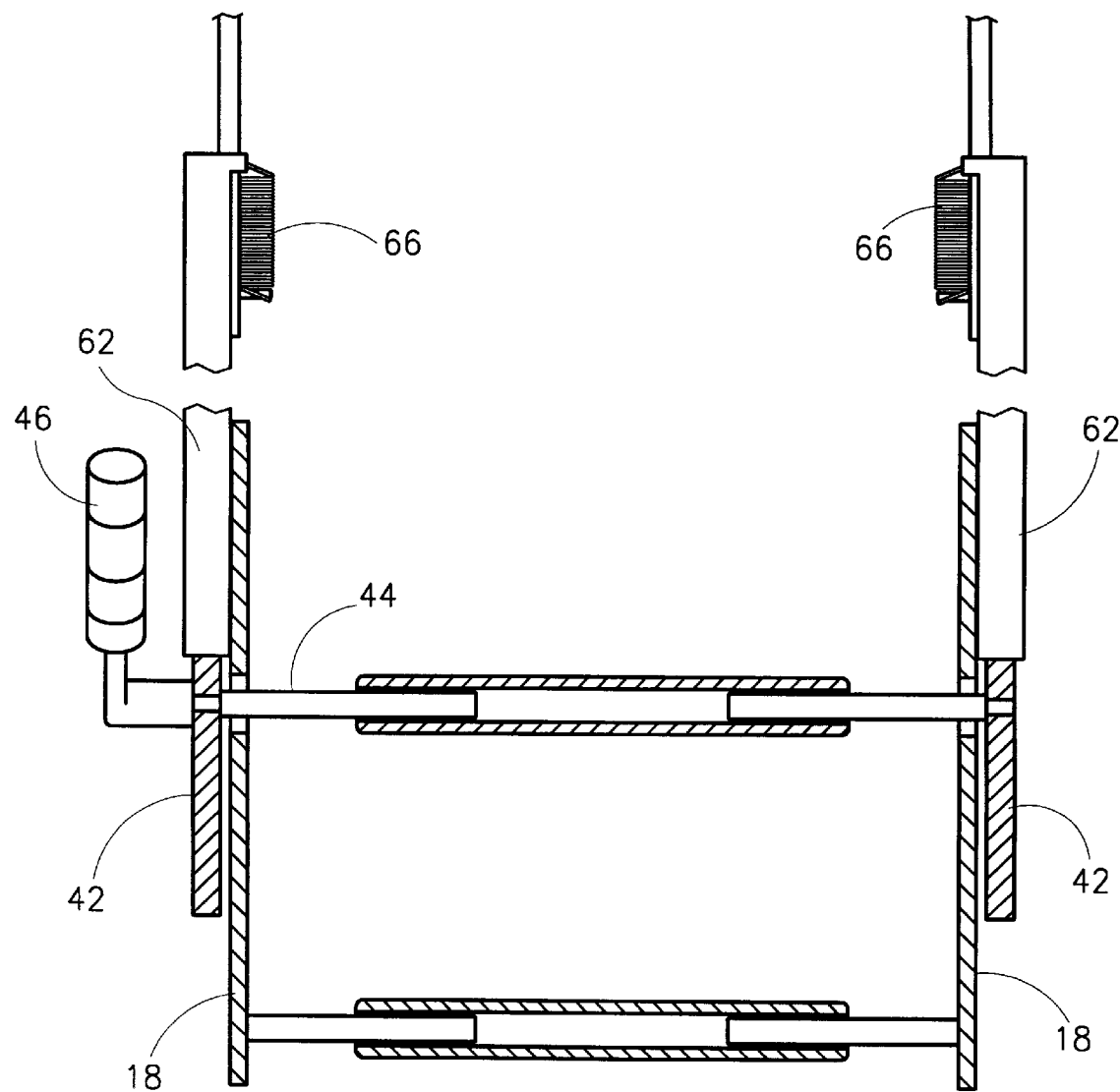
FIGS. 5A and 5B are simplified structural illustrations of the chair mounted device for relieving lower back pressure of FIGS. 4A and 4B in the first and second operative orientations shown respectively in FIGS. 4A and 4B.
Figure 5B:
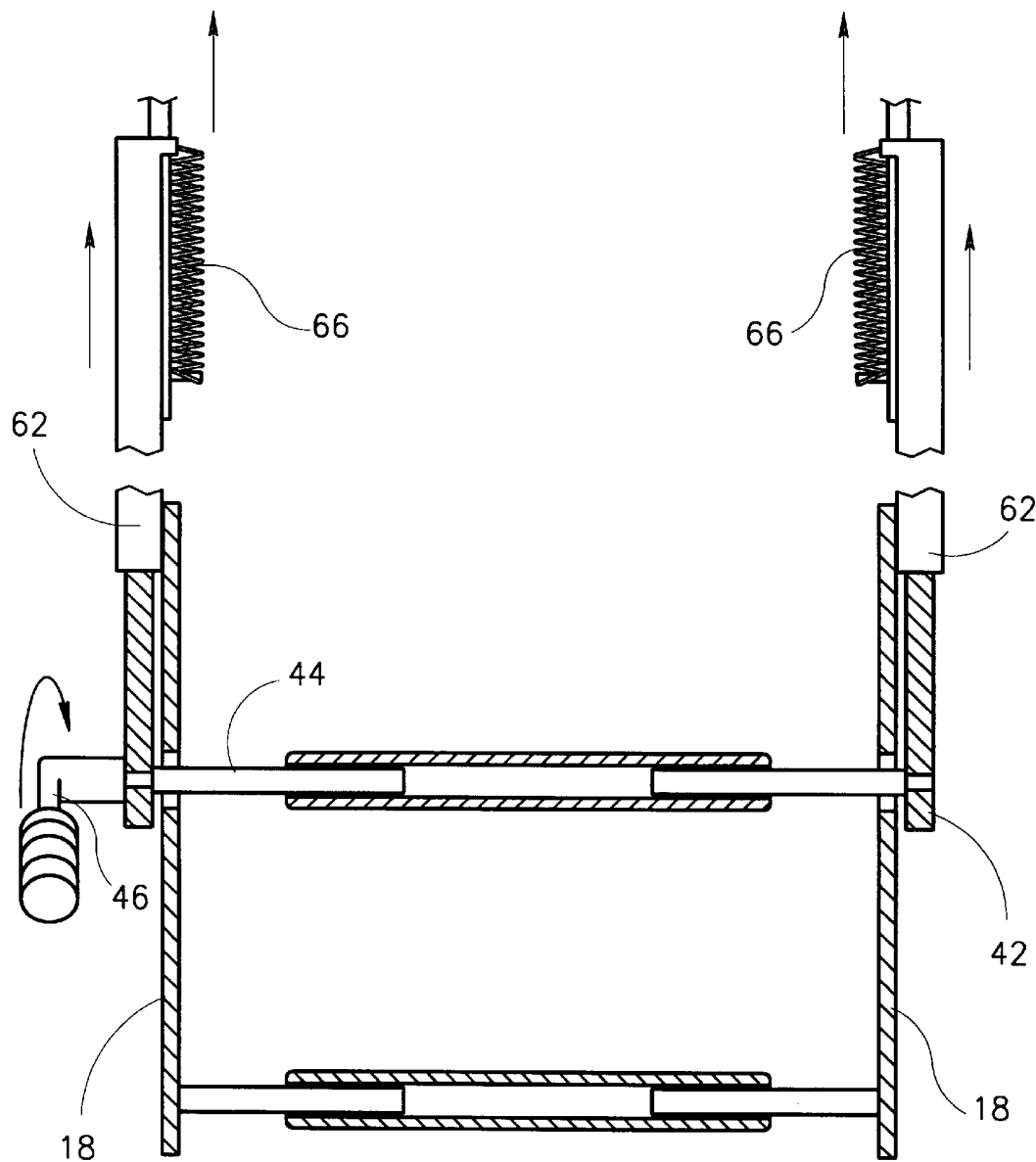

The operation of the apparatus of FIGS. 4A–5B will now be described with reference to the drawings:

Considering an initial state of operation represented by FIGS. 4A and 5A, it is seen that cams 42 are located such that the bottom of each intermediate portion 62 lies on a location "1" on the edge surface of a cam 42. Rotation of lever arm 46 via the ratchet assembly shown in FIGS. 3A–3C causes the cams 42 to rotate about an axis defined by axle 44, thus causing the bottom of each intermediate portion 62 to lie at a location "2" on the edge surface of cam 42. Since location "2" is distanced further from the axis defined by axle 44 than is location "1", the rotation of the cams 42 causes the intermediate portion 62 to be raised relative to the bottom portion 18.

Raising of the intermediate portion 62 causes springs 66 to be tensioned, which applies a raising force to the upper portion 64, causing raising of upper portion 64. Assuming that straps 72 are taut, the tension on the springs 66 applies a raising force on the rib cage of a user engaged by strap assembly 74. It is appreciated that springs 66 are employed to prevent possibly harmful over-tensioning of the user's rib cage and to absorb sudden forces which might otherwise be applied directly to the user's rib cage.

Figure 6:
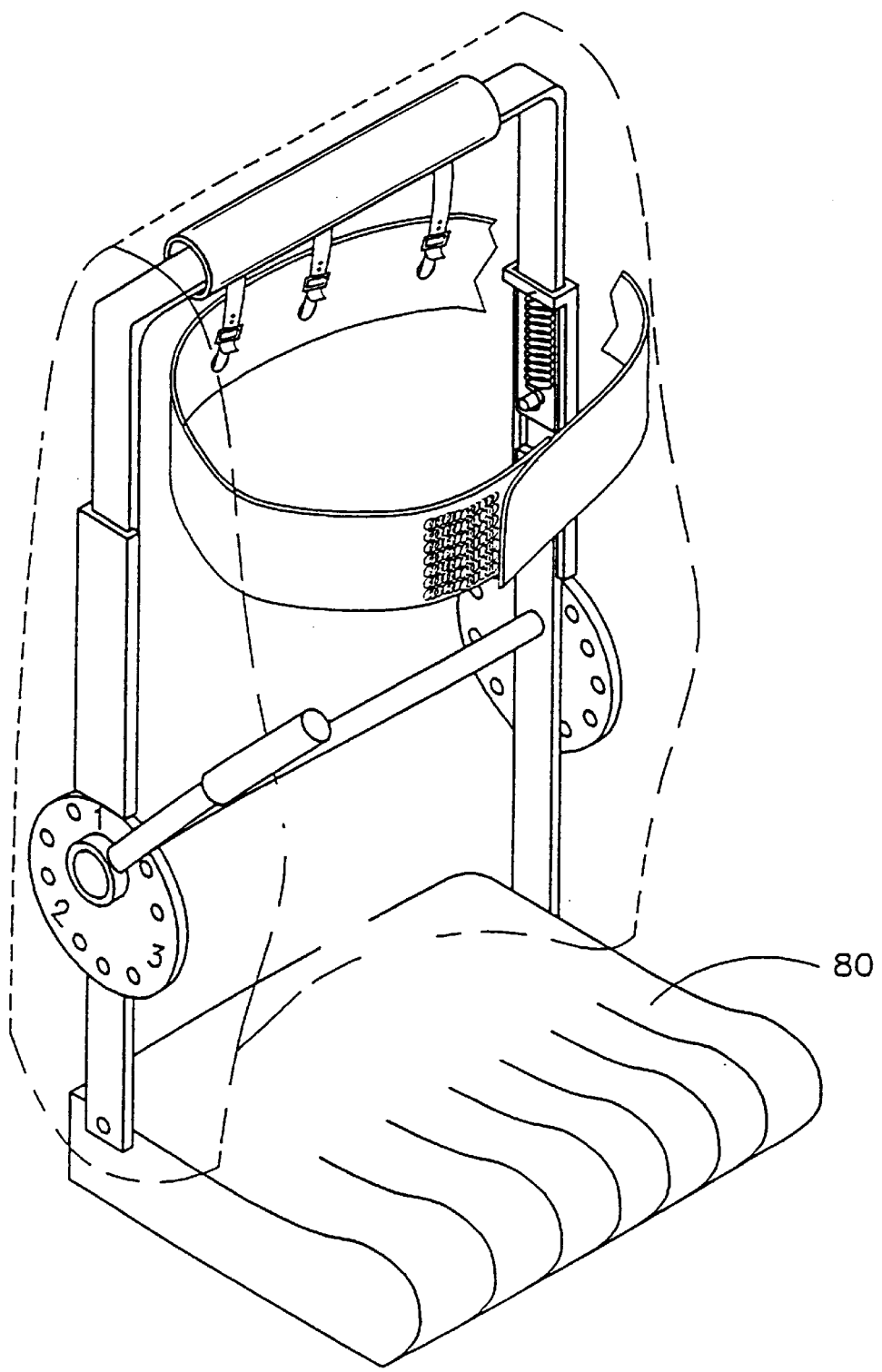
FIG. 6 is a simplified pictorial illustration of another embodiment of the present invention.

Reference is now made to FIG. 6, which illustrates an alternative embodiment of the invention which is incorporated into a seat, such as a vehicle seat 80. Other than being incorporated into a seat, the structure of the apparatus of FIG. 6 may be identical to that shown and described hereinabove with respect to FIGS. 1A–5B.

Figure 7:
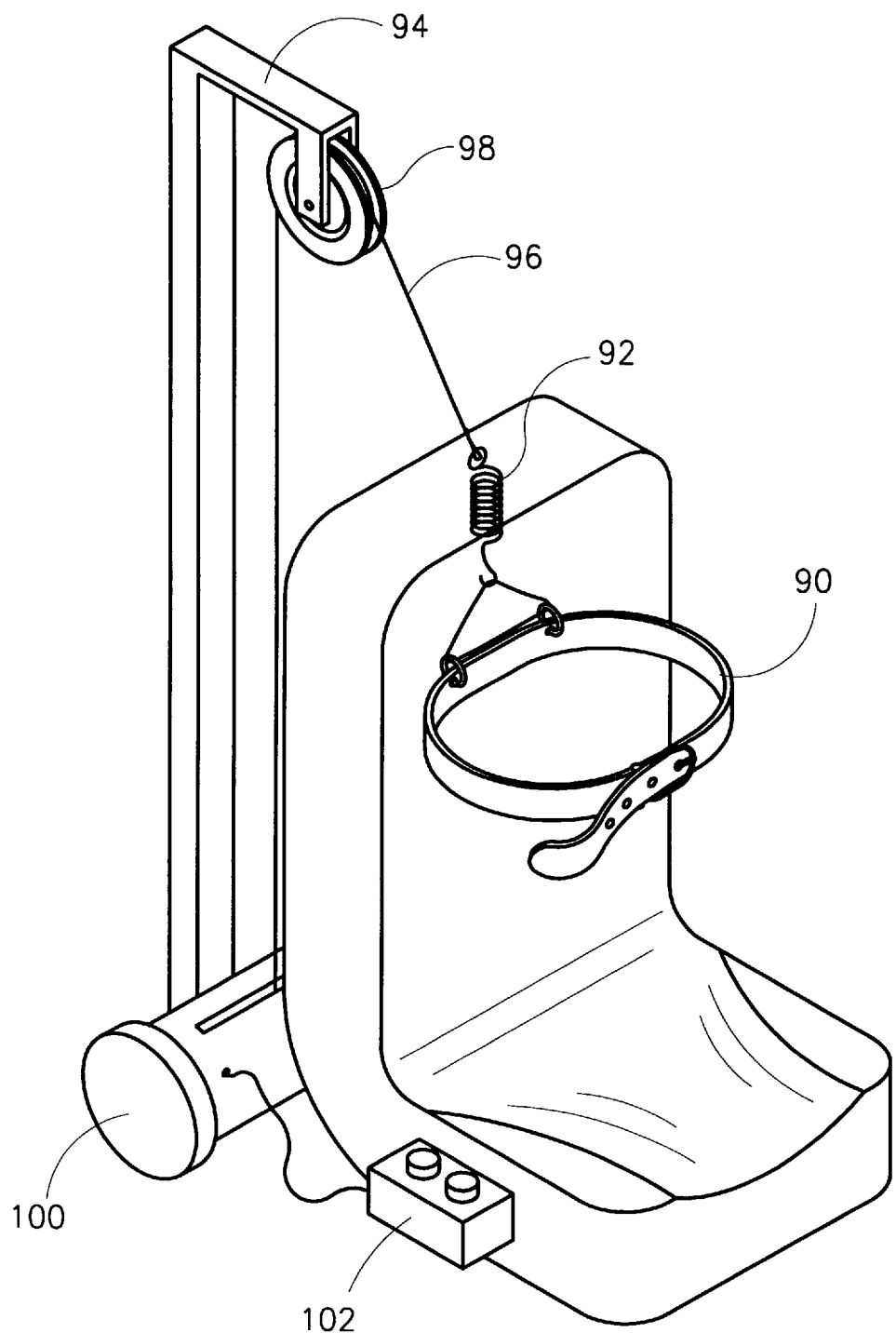
FIG. 7 is a simplified pictorial illustration of yet another embodiment of the present invention.
Figure 8A:
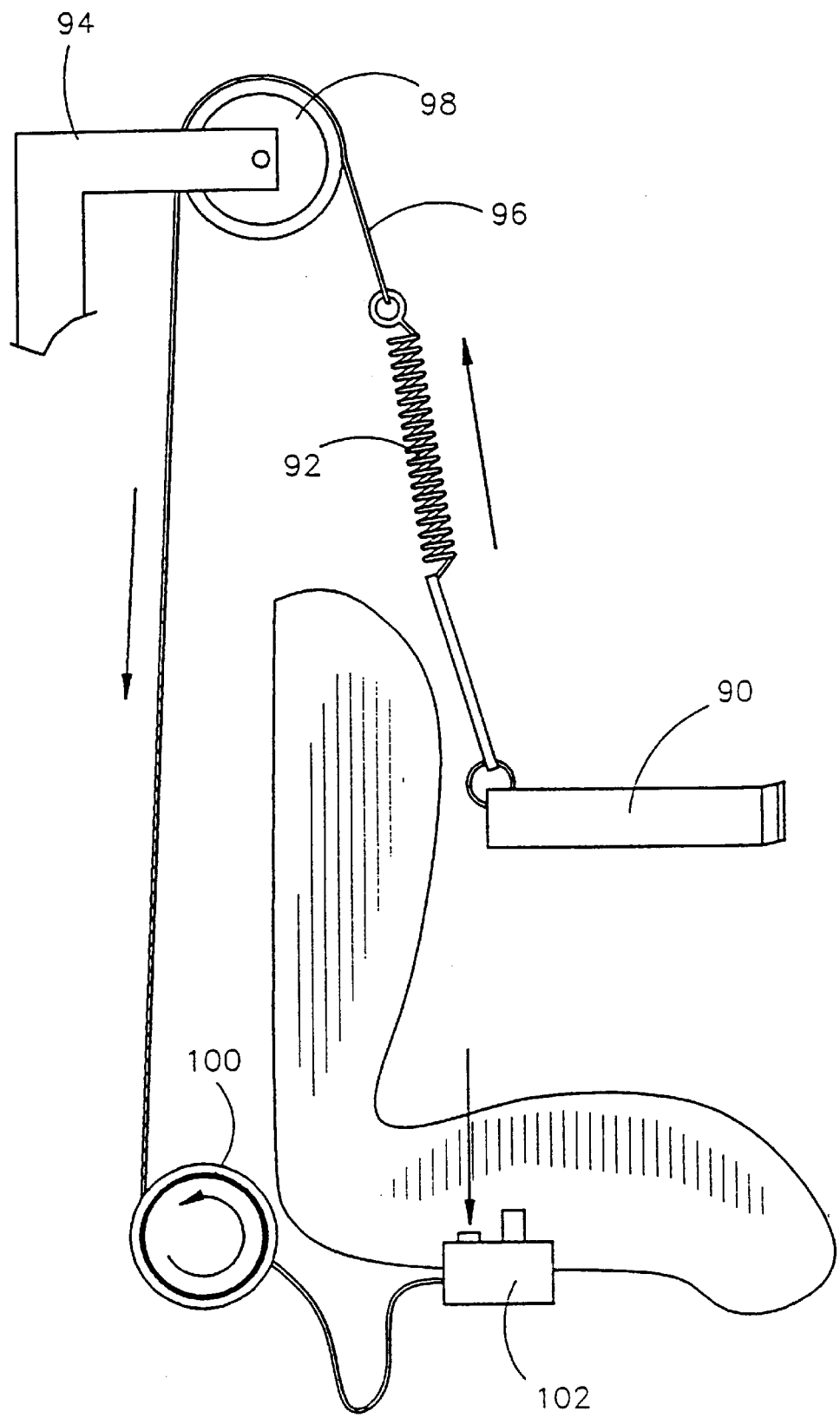
FIGS. 8A and 8B are illustrations of the apparatus of FIG. 7 in respective first and second operative modes.
Figure 8B:
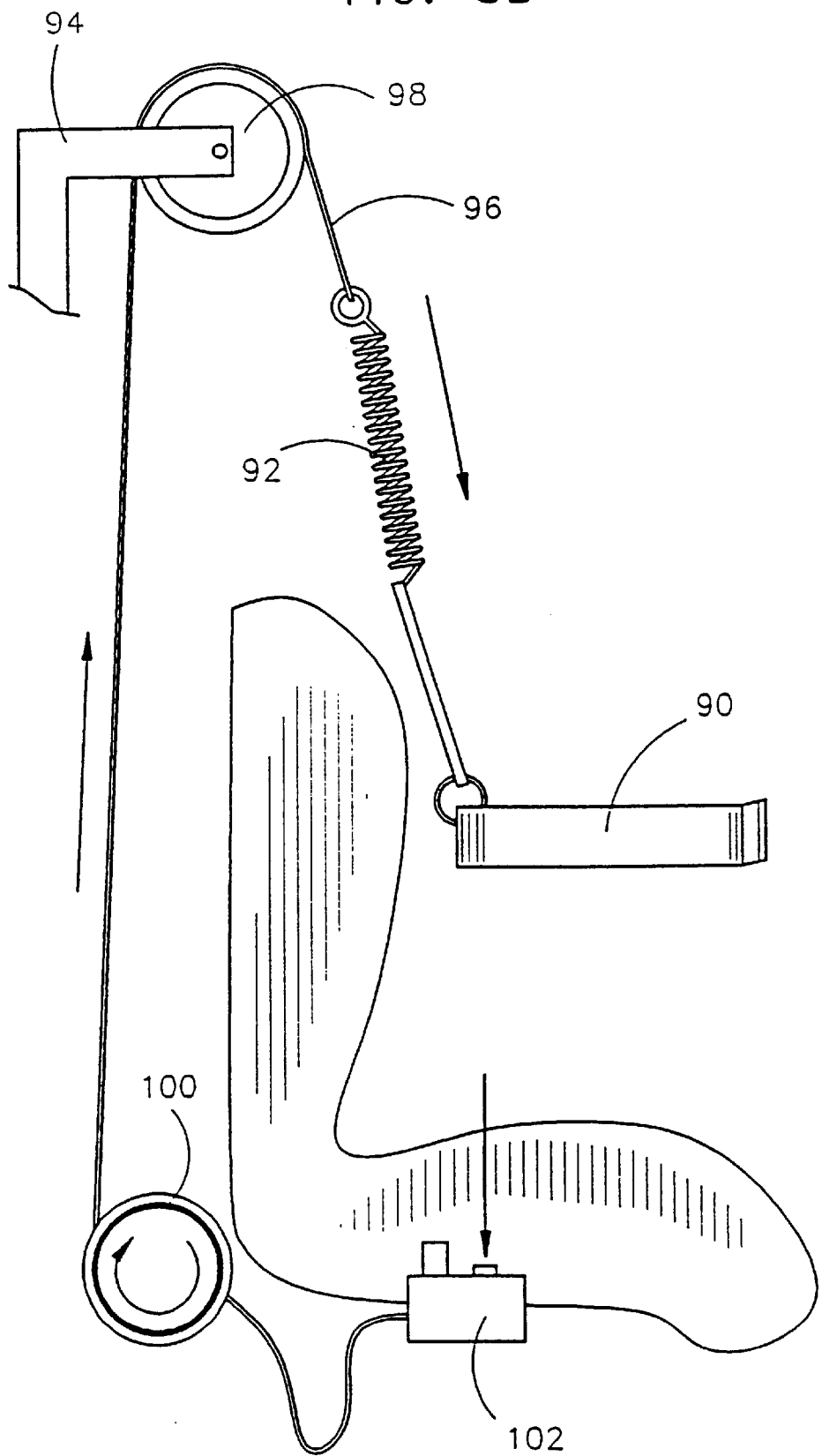

Reference is now made to FIGS. 7, 8A and 8B which illustrate yet another embodiment of the present invention. Here a rib cage engaging belt 90 is supported via a spring 92 on a crane 94 via a cable 96 and pulley 98. The cable is wound or unwound by an electric motor 100 controlled by a user-operated controller 102.

FIG. 8A illustrates the rib cage engaging belt 90 being raised, while FIG. 8B illustrates the rib cage engaging belt 90 being lowered.

Reference is now made to FIGS. 9, 10A, 10B and 10C which illustrate apparatus for relieving lower back pressure, generally designated 200, constructed and operative in accordance with another preferred embodiment of the present invention. Apparatus 200 is arranged to be mounted onto another seat 202 such as a car seat (FIGS. 10A–10C) and comprises a seat element 204 having a bottom portion 206 flexibly connected to a back portion 208.

The bottom portion 206 comprises a raised element 210 connected at one end 212 thereof to a generally flat element 214. Raised element 210 is open at its other end 216 and rests on air cushion 218. At least one coiled spring 220 is preferably inserted between raised element 210 and flat element 214 proximate to end 212. A pump arrangement 222, which is connected via a flexible tube 224 to cushion 218. allows for the release and pumping of air from and into cushion 218.

Back portion 208 is preferably constructed of a rigid material and includes an integrally formed wing component 226 on each side of the back portion 208. Preferably, the internal face of back portion 208 is faced with a soft padding 228. Optionally, adjustable straps 230 can be fitted to each of the wing components 226 to restrain the occupant in seat 204. Straps 230 may be adjusted by any suitable means known in the art such as a "Velcro" type fastening.

Figure 10B:
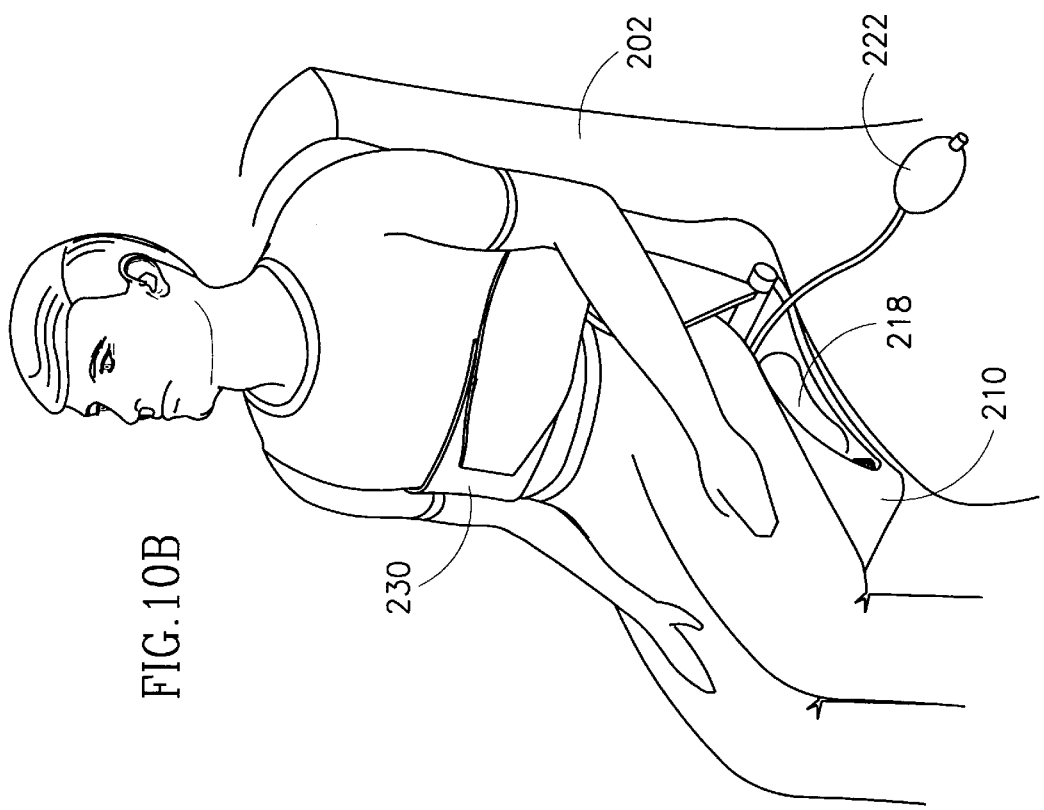
FIGS. 10A–10C are illustrations of the apparatus of FIG. 9 in respective first second and third operative modes.
Figure 10A:
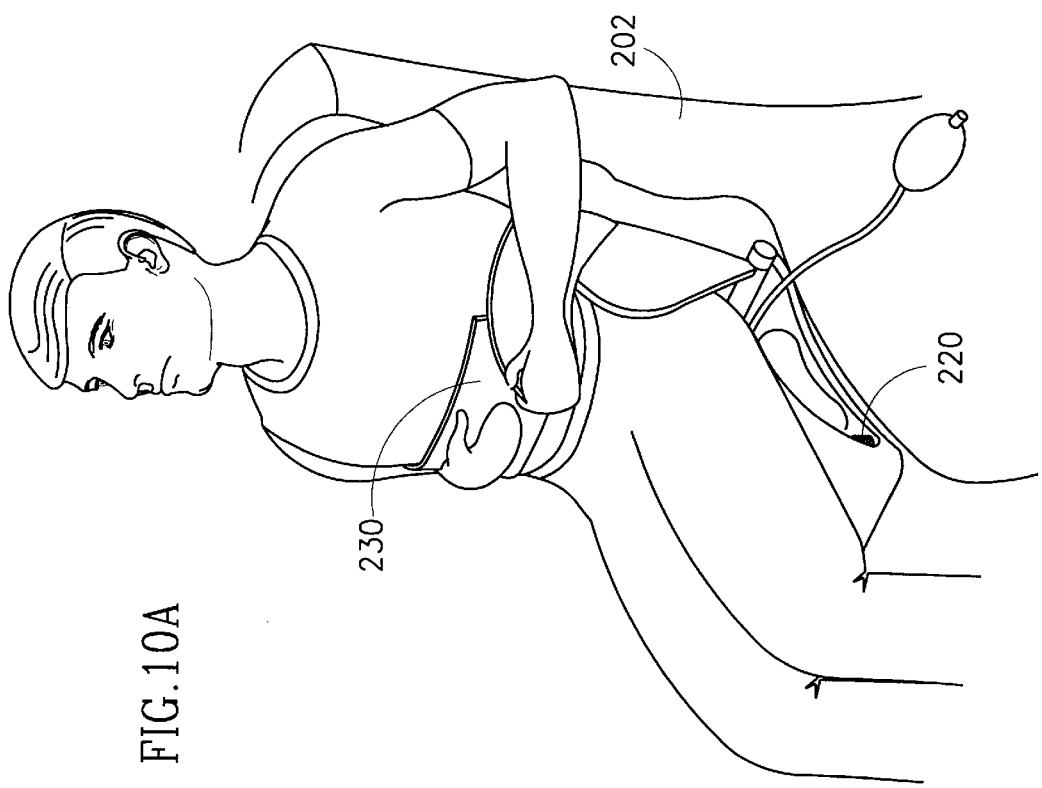
Figure 10C:
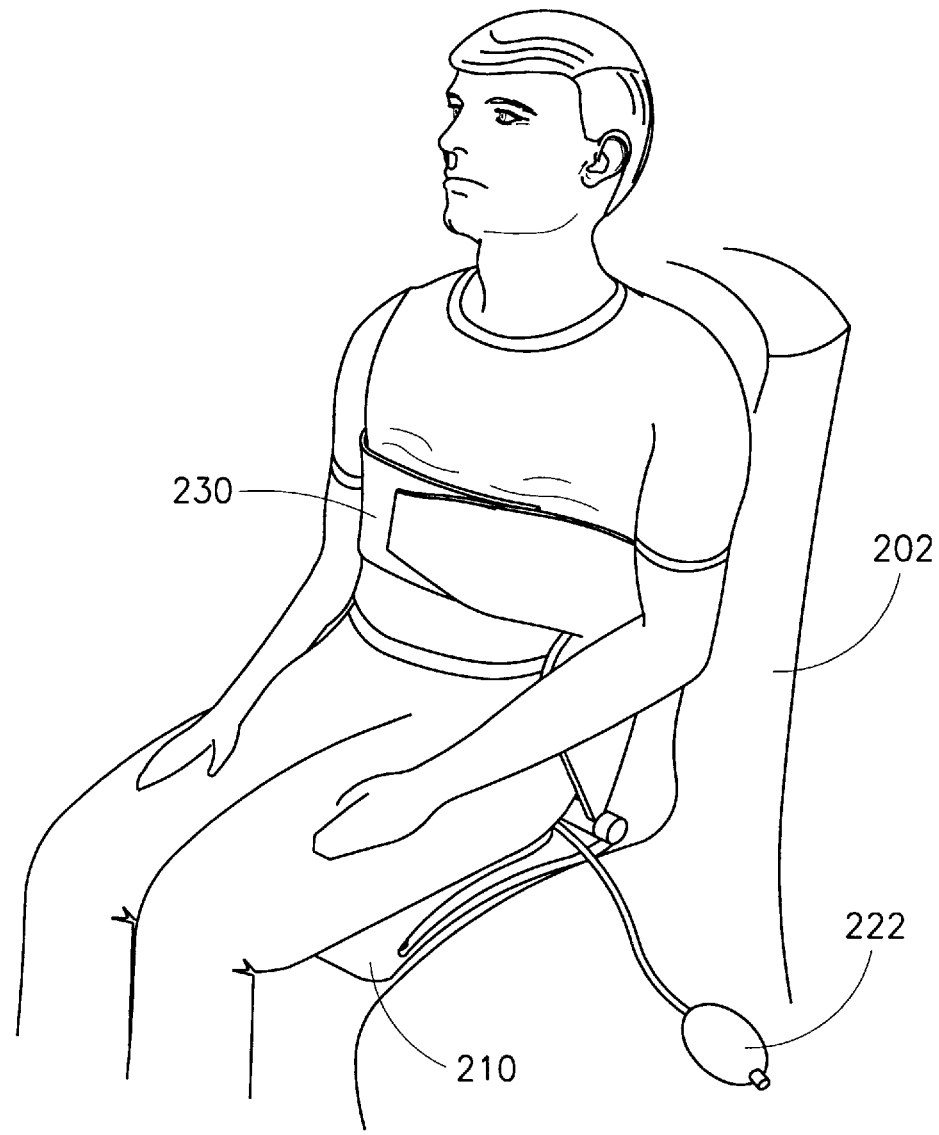

Reference is now made to FIGS. 10A–10C which illustrate the apparatus 200 in respective first second and third operative modes. When not in use, raised element 210 is maintained in a raised position by spring 220. Air cushion 218, which is connected to raised element 210 and is under partial vacuum becomes filled with air through a unidirectional valve (not shown) in pump arrangement 222.

The occupant seats himself on the raised element 210 of the seat 204 causing springs 220 to be tensioned. The occupant tautly fastens straps 230 around his rib cage (FIG. 10A). He can then reduce the height of raised element 210 to a comfortable position by operating pump arrangement 222 to release air from cushion 218 (FIG. 10B). Raising adjustments can be made by operating pump arrangement 222, which changes the volume of air within cushion 218.

The lowering of seat element 210 imparts a raising force on the user's ribs (FIG. 10C). The use of flexible straps 230 prevents possible harmful over-tensioning on the rib-cage.

When the occupant leaves the seat, spring 220 causes raised element 210 to be lifted up and cushion 218 again becomes filled with air.

Reference is now made to FIGS. 11A, 11B, 12A, 12B and 12C which illustrate apparatus for relieving lower back pressure, generally designated 300, constructed and operative in accordance with another preferred embodiment of the present invention.

Figure 11B:
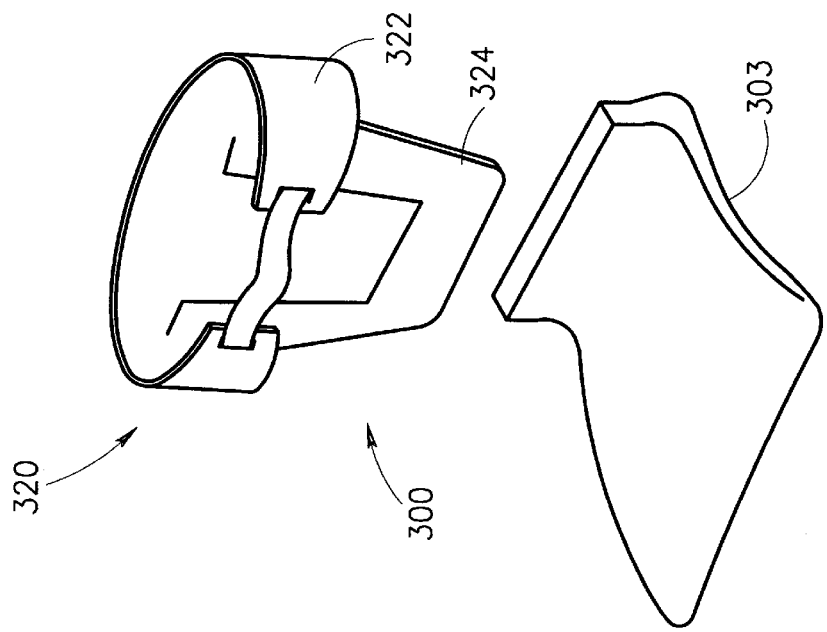
FIGS. 11A and 11B are simplified pictorial illustrations of yet other embodiments of the invention.
Figure 11A:
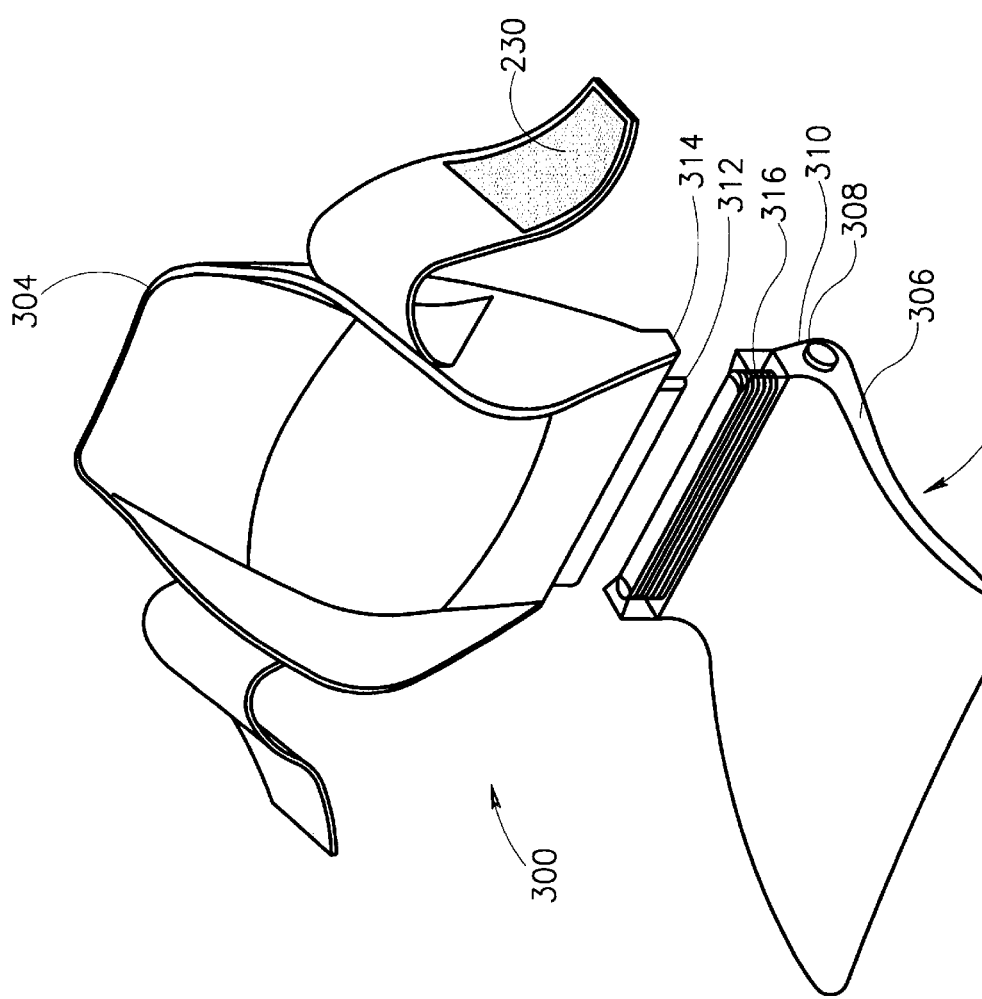

Referring to the embodiment of FIG. 11A, apparatus 300 comprises a bottom portion 302 and a separate back portion 304.

Bottom portion 302 comprises an generally flat element 306 having an upstand 308 integrally formed at its back end 310. A compressible element 316, such as a plurality of coiled springs, are suitably attached to upstand 308.

Back portion 304 comprises a receiving element 312, integrally formed with the lower end 314 of the back portion 304. Receiving element 312 is suitably dimensioned so as to receivably encompass compressible element 316. The height of receiving element 312 is less than the height of compressible element 316 to allow for the compression of element 316.

Figure 12B:
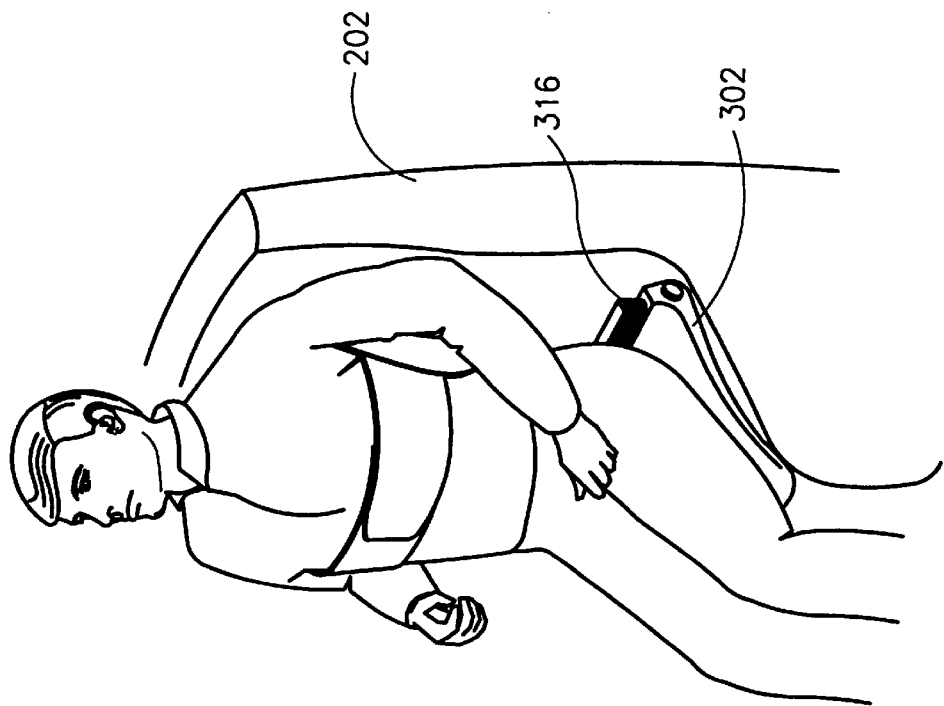
FIGS. 12A–12C are illustrations of the apparatus of FIGS. 11A and 11B in respective first and second operative modes.
Figure 12A:
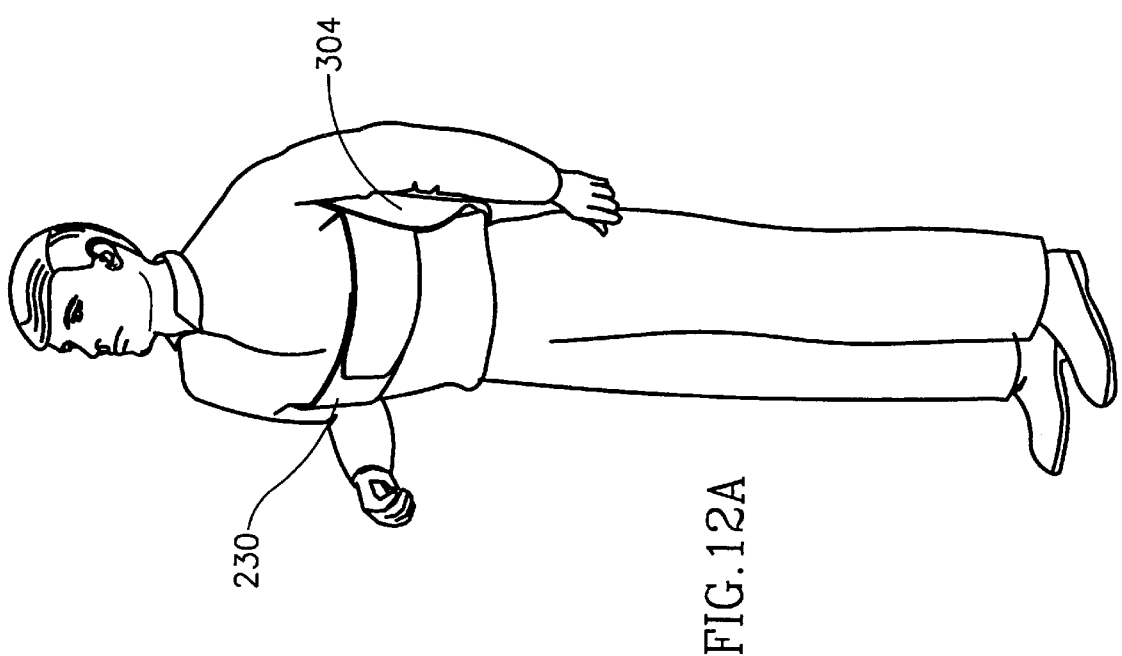
Figure 13:
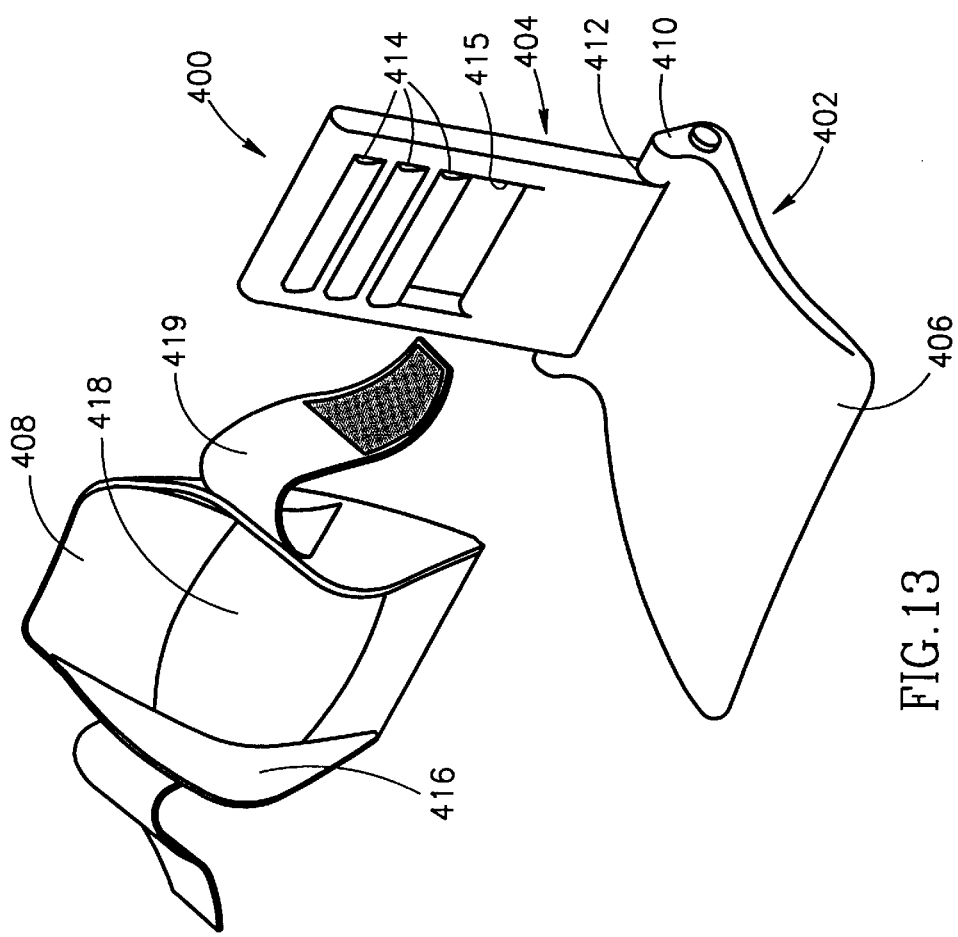
FIG. 13 is a simplified pictorial illustration of yet another embodiment of the present invention.
Figure 12C:
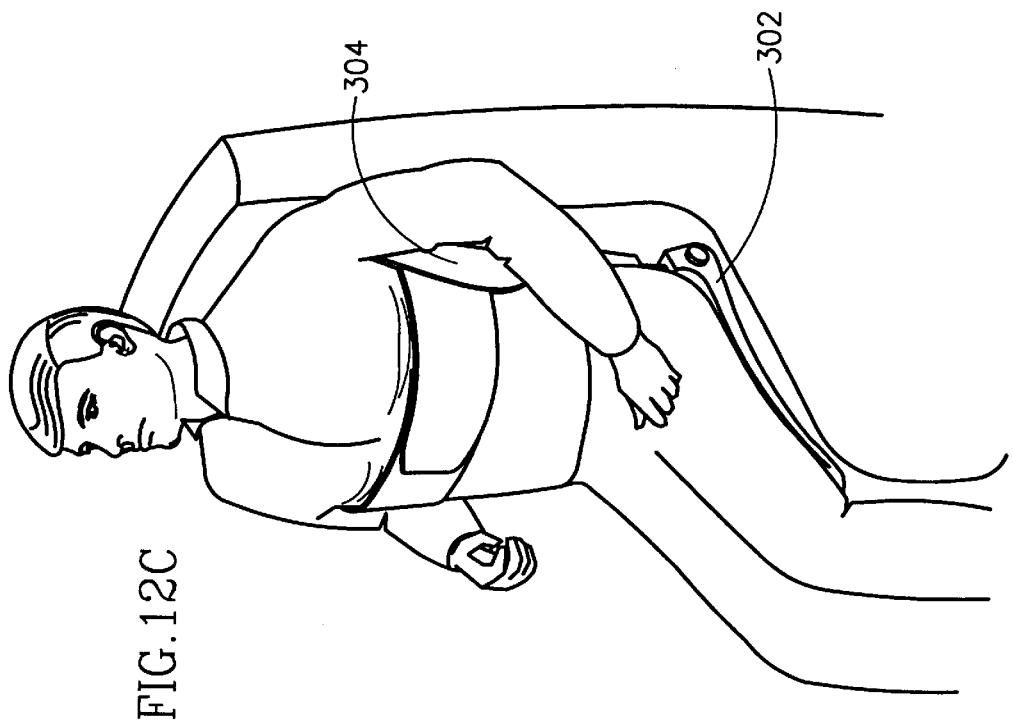

Reference is now made to FIGS. 12A–12C which illustrate the apparatus 300 in operative mode. Initially, the back portion 304 is strapped to the occupant's upper body by means of the adjustable straps 230, as shown in FIG. 12A. The bottom portion 302 is placed in position on the supporting seat 202. The occupant, wearing the back portion 304 lowers himself onto the seat 302 so that the receiving element 312 encompasses compressible element 316 (FIG. 12B).

The engaging of the back portion 304 with the seat portion 302 causes the compression of compressible element 316. The compression imparts a raising force on the user's ribs (FIG. 12C).

It will be appreciated by persons skilled in the art, that the compression of compressible element 316 may be effected by back portion 304 directly making contact with element 316.

Reference is now made to FIG. 11B, which illustrates an alternative embodiment of apparatus 300. In this embodiment, the apparatus comprises a bottom portion 303 and a back portion 320 which comprises adjustable straps 322 integrally formed with a rigid or semi-rigid projecting component 324.

In operation, back portion 320 is strapped to the occupant's rib cage by means of the adjustable straps 322 (similar to FIG. 12A). The bottom portion 303 is placed in position on the supporting seat 202. The occupant, wearing the back portion 320 lowers himself onto the seat 303. Projecting component 324 engages bottom portion 303. The contact of projecting component 324 with bottom portion 303 pushes projecting component 324 upwards and imparts a raising force on the user's rib cage (similar to FIG. 12C). In an alternative embodiment, projecting component 324 engages seat 202 itself obviating seat portion 303.

It will be appreciated to persons knowledgeable in the art, that the embodiment of FIG. 11B is particularly suitable for motorbike riders and the like who, only need to strap back portion 320 to their upper body. The action of sitting on the seat pushes projecting component 324 upwards and imparts a raising force on the user's ribs.

Reference is now made to FIGS. 13, 14A, 14B and 14C which illustrate apparatus for relieving lower back pressure, generally designated 400, constructed and operative in accordance with another preferred embodiment of the present invention.

Apparatus 400 comprises a seat support element 402 located on a seat and preferably comprising a back portion 404 pivotally connected to a bottom portion 406. Apparatus 400 further comprises a rib cage assembly 408.

Bottom portion 406 is generally flat having a raised upstand 410, integrally formed with the back end 412 thereof.

Back portion 404 is a generally rectangular in shape and comprises a plurality of "upwardly sloping" integrally formed slats 414. An aperture 415 is molded within back portion 404 and is located approximately in the center of back portion 404 proximate to the lower of plurality of integrally formed slats 414. Back portion 404 is pivotally connected at one end to the raised upstand 410. Preferably, the pivot connection includes a spring-like device (not shown) so that back portion 404 maintains an acute angle with bottom portion 406 (FIG. 14B).

Rib cage assembly 408 is preferably constructed of a rigid material. Rib cage assembly 408 includes integrally formed wing component 416 on each side of the rib cage assembly 408. Preferably, the internal face of rib cage assembly 408 is faced with a soft padding 418. Optionally, adjustable straps 419 can be fitted to each of the wing components 416 to restrain the occupant to rib cage assembly 408. Straps 419 may be adjusted by any suitable means known in the art such as a "Velcro" type fastening.

Figure 14A:
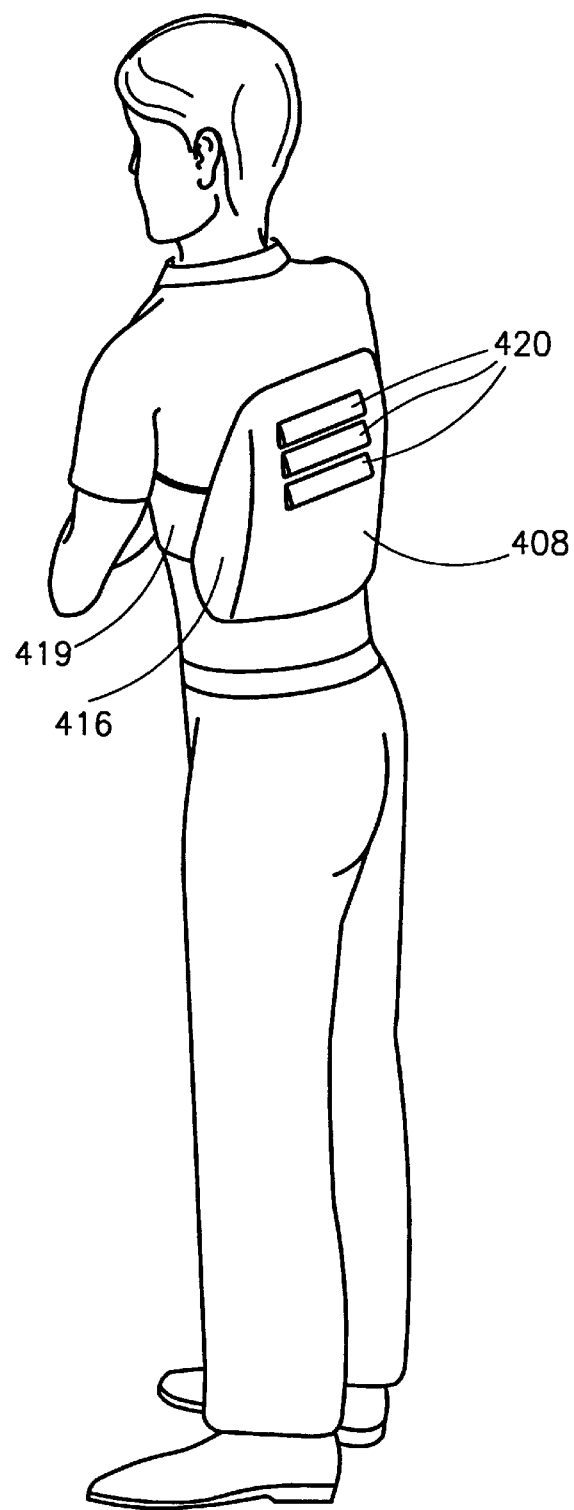
FIGS. 14A–14C are illustrations of the apparatus of FIG. 13 in respective first second and third operative modes.

As best seen in FIG. 14A, rib cage assembly 408 further comprises a plurality of "downwardly sloping" ribs 420. The plurality of ribs 420 are integrally formed on the external face thereof. The "downwardly sloping" ribs 420 are similarly dimensioned to the plurality of "upwardly sloping" integrally formed slats 414, so that they may connectably engage each other.

Figure 14C:
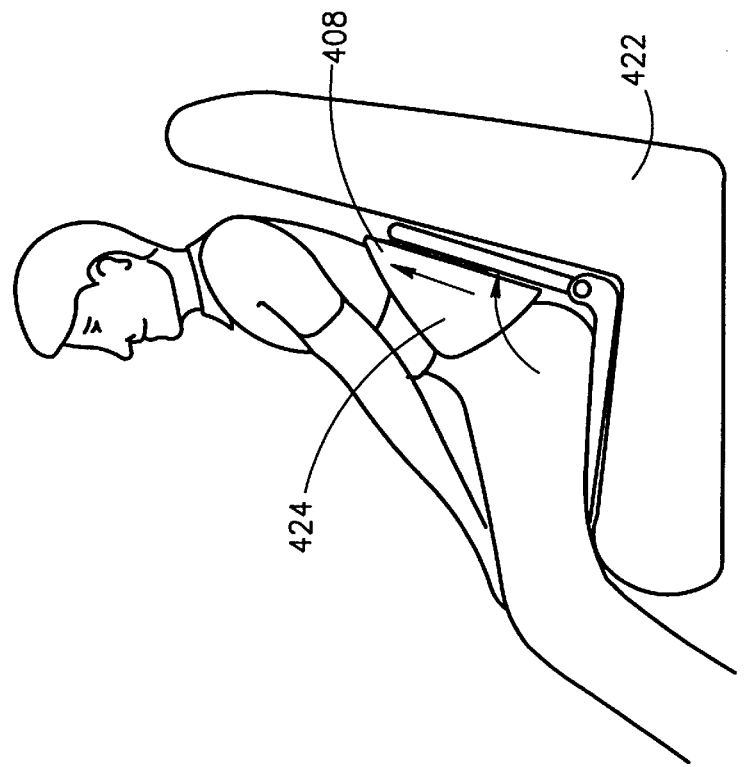
Figure 14B:
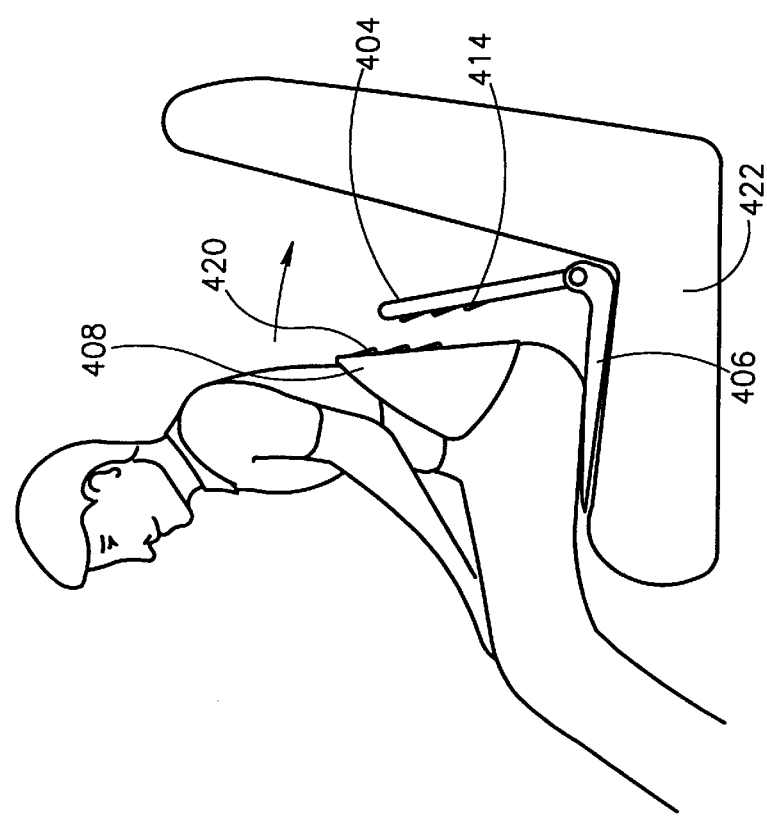

Reference is now made to FIGS. 14A–14C which illustrate the apparatus 400 in operative mode. Initially, the rib cage assembly 408 is strapped to the occupant's upper body by means of the adjustable straps 419, as shown in FIG. 14A. Seat support element 402 is placed in position on the supporting seat 422. As best seen in FIG. 14B, the occupant, wearing the rib cage assembly 408 bends forward and lowers himself onto the bottom portion 406 and positions himself so that the plurality of ribs 420 on the external face of rib cage assembly 408 engages the plurality of integrally formed slats 414 of the back portion 404.

As the user leans back against the supporting seat 422 and sits up straight, the relative motion between rib cage assembly 408 and slats 414 imparts a raising force to the user's ribs, indicated by arrow 424 (FIG. 14C).

Figure 16:
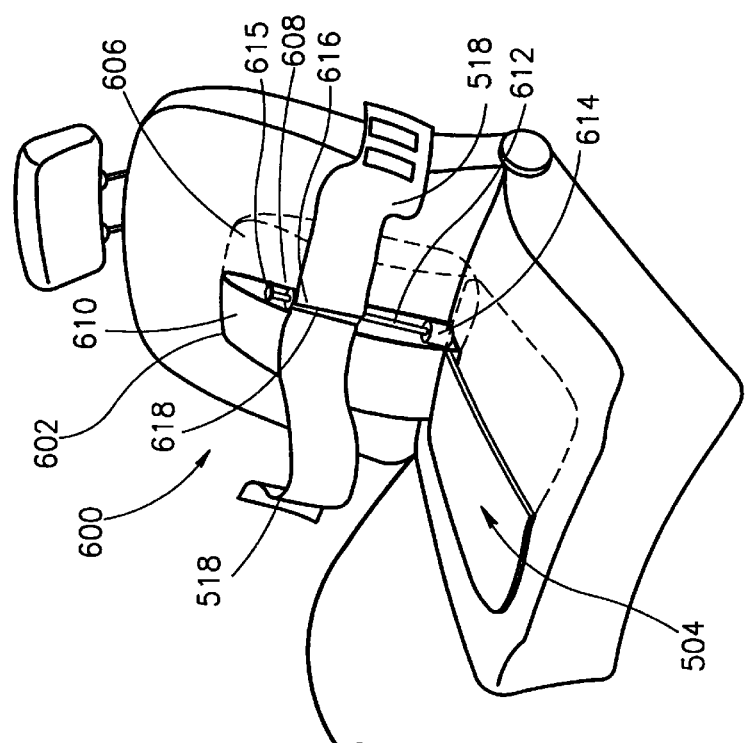
FIG. 16 is a simplified pictorial illustration of yet another embodiment of the present invention.
Figure 15:
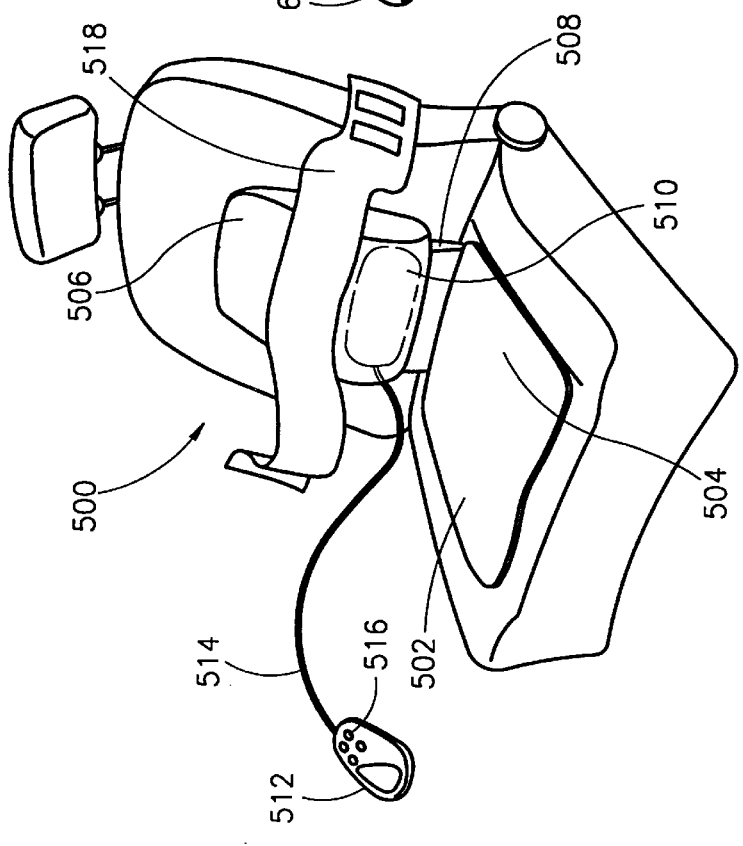
FIG. 15 is a simplified pictorial illustration of yet another embodiment of the present invention.

Reference is now made to FIGS. 15 and 16 which illustrate apparatus for relieving lower back pressure, generally designated 500 and 600, respectively, constructed and operative in accordance with other preferred embodiments of the present invention.

FIG. 15 illustrates the use of compressed air operating means for relieving lower back pressure.

Apparatus 500 comprises a seat support element 502 having a bottom portion 504 connected to a back portion 506. Bottom portion 504 is generally flat having a raised upstand 508, integrally formed with the back end thereof. Back portion 506 comprises an air cushion 510. An air compressor 512 is connected via a flexible tube 514 to cushion 510. Air compressor 512 is any known in the art compressor connected to suitable controls 516 to allow for the entry and release of air from cushion 510.

Back portion 506 further comprises adjustable straps 518 for firmly securing the occupant's upper body to back portion 506, as described hereinabove. Adjustable straps 518 are suitably attached to the top of air cushion 510.

In operation, the air cushion 510 is deflated and the occupant sits on seat support element 502 and fastens adjustable straps 518 around his rib cage. By adjustable use of controls 516, the occupant can regulate the compressor 512 to inflate air cushion 510. By increasing the amount of air within the cushion 510 lifts straps 518 thereby exerting pressure on the lower back of the restrained occupant.

Figure 9:
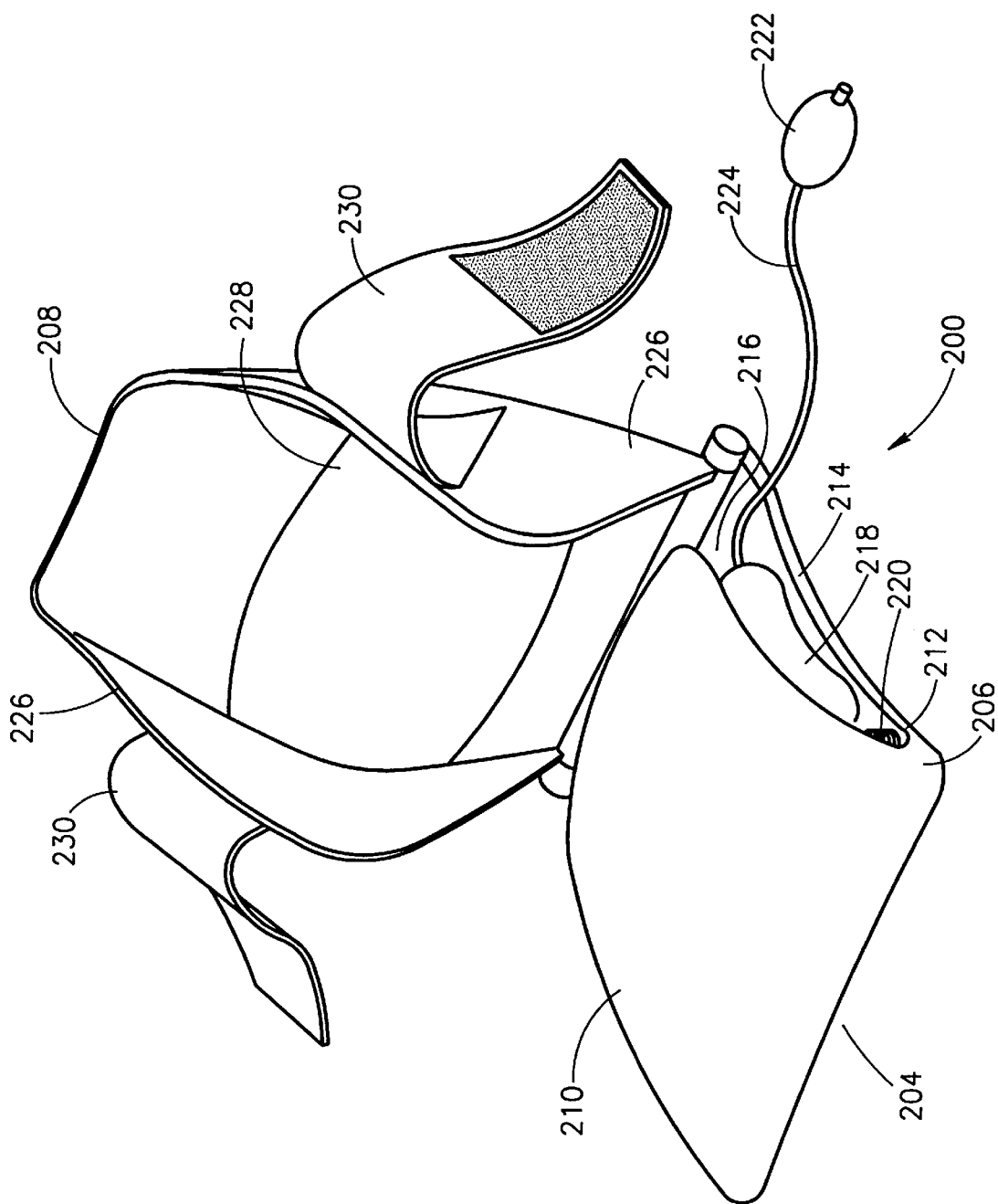
FIG. 9 is a simplified pictorial illustration of another embodiment of the invention.

It will be appreciated by persons skilled in the art that air can be manually entered or released by means of any suitable arrangement such as the valve arrangement described with reference to the embodiment of FIGS. 9–10. It will also be appreciated that other suitable means replacing cushion 510, such as the use of hydraulic pistons may be used.

FIG. 16 illustrates the use of an electric motor to selectably impart an upward pressure to an user's rib cage.

FIG. 16 is generally similar to apparatus 500 described hereinabove with reference to FIG. 15. Elements having similar components are similarly designated and are not further described.

Apparatus 600 comprises a seat support element 602 having a bottom portion 504 connected to a back portion 606. Back portion 606 comprises an lead screw device 608 enclosed within padding 610. Lead screw device 608 comprises a lead screw 612 attached to a motor 614 at its lower end and freely restrained at its top end by mount 615. Mount 615 is suitably connected to padding 610 to allow screw 612 to freely rotate along a generally vertical axis. A nut 616 is threaded onto lead screw 612 and a plate 618 is welded or otherwise suitably connected to nut 616.

Back portion 606 further comprises adjustable straps 518 for firmly securing the occupant's upper body to back portion 606, as described hereinabove. Adjustable straps 518 are attached to plate 618. Thus, rotation of lead screw 612 causes nut 616 to rise or fall, thereby causing the attached straps 518 to also move up or down and release lower back pressure.

Motor 614, which may be an electric motor or similar device, is connected to and operable by a suitable switch device 620, such as a three-way switch.

In operation, the occupant lowers screw 612 to a non-tensioning position. The occupant sits on seat support element 602 and fastens adjustable straps 518 around his rib cage. By use of switch 620, the occupant can operatably cause screw 612 to rotate clockwise or anti-clockwise. The rotation of screw 612 causes nut 616 to rise or fall thereby causing straps 518, around the occupant, to rise up or down. Lifting the straps 518 raises the rib cage of the occupant relative to his lower body so as to release lower back pressure.

Figure 17:
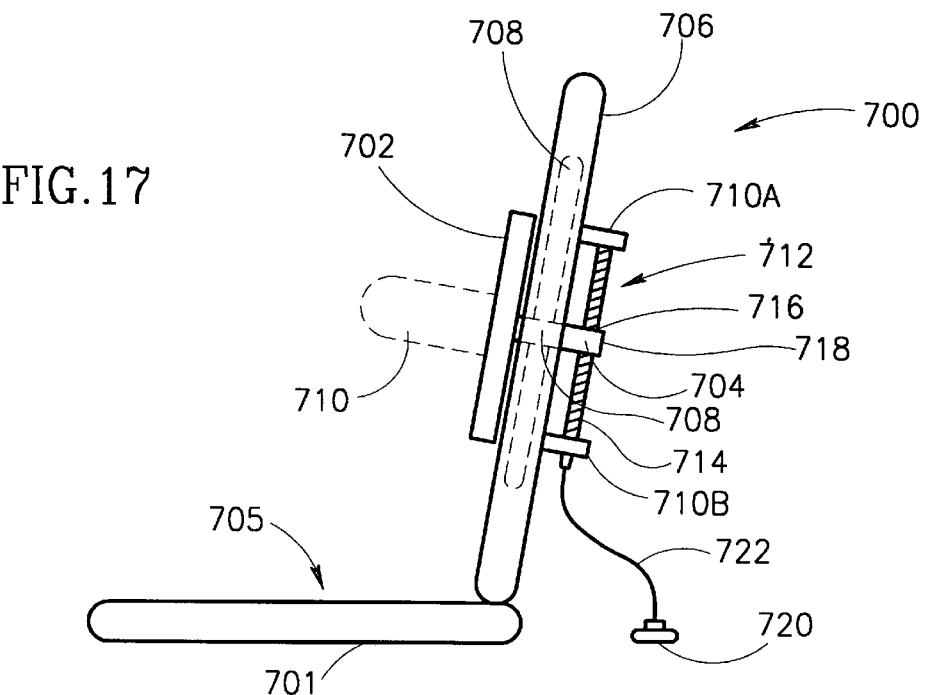
FIG. 17 is a simplified pictorial illustration of yet another embodiment of the present invention.
Figure 18:
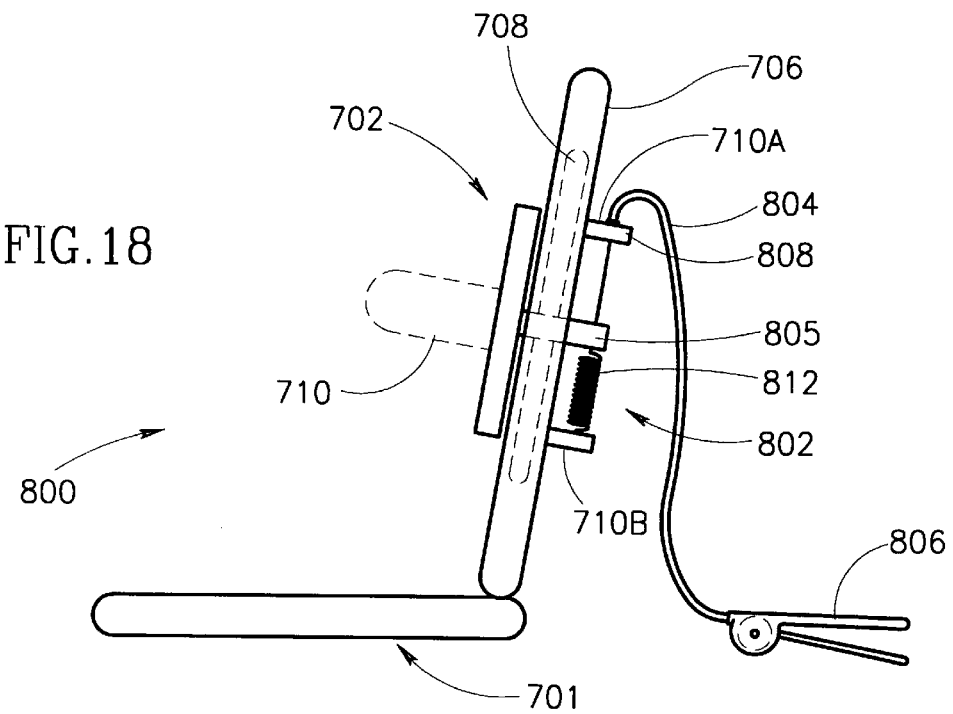
FIG. 18 is a simplified pictorial illustration of yet another embodiment of the present invention.

Reference is now made to FIGS. 17 and 18 which illustrate apparatus for relieving lower back pressure, generally designated 700 and 800, respectively, constructed and operative in accordance with other preferred embodiments of the present invention.

The embodiments of FIGS. 17 and 18, comprise a seat support element 701 and an adjustable rib cage component 702 having a member 704 extending from the back thereof. Seat support element 701 comprises a bottom portion 705 connected to a back seat support element 706. A slot 708 is formed in the back seat support element 706 to allow member 704 to move in a generally vertical direction. Member 704 which may be hollow, for example a nut, generally similar to nut 616, described with reference to the embodiment of FIG. 16, or alternatively, member 704 may be solid such as component designated 805 (described hereinbelow FIG. 18). Member 704 extends beyond the back seat support element 706. Upper and lower support members, 710a and 710b are attached to back seat support element 706 either side of member 704.

Rib cage component 702 comprises adjustable straps 710 for firmly securing the occupant's upper body, generally similar to the straps described hereinabove.

The apparatuses 700 and 800 of FIGS. 17 and 18, respectively further comprise raising mechanisms generally designated 712 and 802, respectively, which will be separately described.

Referring now to FIG. 17, raising mechanism 712 comprises a lead screw 714 which is threaded through nut 704 and is freely supported at either end by upper and lower support members, 710a and 710b, respectively. An operating device 720 for rotating screw 714 is attached via a suitable semi-flexible cable 722 to screw 714. A suitable control is attached to cable 722 for operatably controlling the rotation of screw 714.

The rotation of screw 714 causes the rise and fall of nut 704 which adjustably raises (or lowers) rib cage component 702. To raise the occupant's rib cage, the occupant sits on the seat, lowers rotating screw 714 so that it is in a non-tensioning position. The occupant fastens the adjustable straps 710 around his rib cage. By rotating the screw 714 and lifting the nut 704, upward tension is applied via the adjustable straps 710 to the user's rib cage so as to release lower back pressure.

Referring now to FIG. 18, raising mechanism 802 comprises a tensioning cable 804 coupled at one end thereof to a tensioning device 806. One end of tensioning cable 804 extends below upper support member 710a and is coupled to component 805. A return spring 812, is attached at one end to lower support member 710*b* and at its other end to component 805.

By manually applying pressure to tensioning device 806, the occupant can operate mechanism 802 to raise rib cage component 702. Tensioning device 806 operates in a manner generally similar to the gearing system on a bicycle, whereby pressure on tensioning device 806 increases the strain on tensioning cable 804. The tensioning of cable 804 is transferred via component 805 (member 704) thereby to raise rib cage component 702. Since the occupant is restrained by the adjustable straps 710, the occupant's rib cage is also raised. The raising of component 805 increases the strain on return spring 812.

It will appreciated by persons skilled in the art that any or all of the various devices and mechanisms described hereinabove with reference to a particular embodiment are also applicable to any of the other embodiments. That is, any of the user controlled tensioning devices may be used with different rib cage assemblies. For example, the motor 614 of FIG. 16 may also be used with the embodiments of FIGS. 17 or 18.

It will appreciated by persons skilled in the art that invention is not limited by what has been particular shown and described hereinabove. Rather the scope of the present invention is defined only by the claims which follow:

We claim:

1. A portable seat supportable apparatus for relieving lower back pressure of a user comprising:
   a) a seat portion arranged to be supported on a seat and be sat upon by the user;
   b) a rib cage engagement assembly arranged to removeably engage the rib cage of the user when he is sitting on said seat portion; and
   c) user controlled tensioning apparatus for selectably applying tension between said rib cage engagement assembly and said seat portion, thereby to relieve lower back pressure of said user;
   wherein said seat portion comprises a bottom portion connected to a back portion;
   and wherein said user controlled tensioning apparatus comprises:
      i) upper and lower support members attached to said back portion;
      ii) a lead screw freely supported at each end by said upper and lower support members;
      iii) a nut threaded onto said lead screw, said nut being attached to said rib cage engagement assembly; and
      iv) an operating device for rotating said screw.

2. A portable seat supportable apparatus for relieving lower back pressure of a user comprising:
   a) a seat portion arranged to be supported on a seat and be sat upon by the user;
   b) a rib cage engagement assembly arranged to removeably engage the rib cage of the user when he is sitting on said seat portion; and
   c) user controlled tensioning apparatus for selectably applying tension between said rib cage engagement assembly and said seat portion, thereby to relieve lower back pressure of said user;
   wherein said seat portion comprises a bottom portion connected to a back portion;
   and wherein said user controlled tensioning apparatus comprises:
      i) upper and lower support members attached to said back portion;
      ii) a third support member attached to said rib cage engagement assembly;
      iii) a tensioning cable coupled at one end thereof to said third support member and coupled to said upper support member; and
      iv) an operating device for applying tension to said tensioning device.

3. A portable seat supportable apparatus for relieving lower back pressure of a user comprising:
   a) a seat portion arranged to be supported on a seat and be sat upon by the user;
   b) a rib cage engagement assembly arranged to removeably engage the rib cage of the user when he is sifting on said seat portion; and
   c) user controlled tensioning apparatus for selectably applying tension between said rib cage engagement assembly and said seat portion, thereby to relieve lower back pressure of said user;
   wherein said seat portion comprises a bottom portion connected to a back portion;
   wherein said user controlled tensioning apparatus comprises means for altering the position of said rib cage assembly relative to said bottom portion thereby applying tension;
   and wherein said user controlled tensioning apparatus comprises:
      i) upper and lower support members attached to said back portion;
      ii) a lead screw freely supported at each end by said upper and lower support members;
      iii) a nut threaded onto said lead screw, said nut being attached to said rib cage engagement assembly; and
      iv) an operating device for rotating said screw.

4. A portable apparatus for relieving lower back pressure of a user, comprising:
   a) a portable seat portion arranged to be supported on a seat, said portable seat portion comprising a bottom portion and a back portion; and
   b) a rib cage engagement assembly arranged to removably engage the rib cage of said user, said rib cage engagement assembly being connected to said back portion;
   c) means for moving said rib cage relative to said back portion when said user is sitting thereon; and
   d) user controlled tensioning apparatus for selectable applying tension between said rib cage engagement assembly and said bottom portion, thereby to relieve lower back pressure of said user,
   and wherein said user controlled tensioning apparatus comprises:
      i) upper and lower support members attached to said back portion;
      ii) a lead screw freely supported on each end by said upper and lower support members;
      iii) a nut threaded onto said lead screw, said nut being attached to said rib cage engagement assembly; and
      iv) an operating device for rotating said screw.

5. A portable apparatus for relieving lower back pressure of a user, comprising:
   a) a portable seat portion arranged to be supported on a seat, said portable seat portion comprising a bottom portion and a back portion; and
   b) a rib cage engagement assembly arranged to removably engage the rib cage of said user, said rib cage engagement assembly being connected to said back portion;
   c) means for moving said rib cage relative to said back portion when said user is sitting thereon; and d) user controlled tensioning apparatus for selectable applying tension between said rib cage engagement assembly and said bottom portion, thereby to relieve lower back pressure of said user, and wherein said user controlled tensioning apparatus comprises:
   i) upper and lower support members attached to said back portion;
   ii) a third support member attached to said rib cage engagement assembly;
   iii) A tensioning cable coupled at one end thereof to said third support member and coupled to said upper support member; and
   iv) an operating device for applying tension to said tensioning cable.

6. A portable apparatus for relieving lower back pressure of a user, comprising:
   a) a portable seat portion arranged to be supported on a seat, said portable seat portion comprising a bottom portion and a back portion; and
   b) a rib cage engagement assembly arranged to removably engage the rib cage of said user, said rib cage engagement assembly being connected to said back portion;
   c) means for moving said rib cage relative to said back portion when said user is sitting thereon; and
   d) user controlled tensioning apparatus for selectable applying tension between said rib cage engagement assembly and said bottom portion, thereby to relieve lower back pressure of said user;

and wherein said raising means comprises:
   i) inflatable means connected to said rib cage engagement assembly;
   ii) a lead screw device attached to a motor at one end thereof and freely rotatable at its other; and
   iii) a nut threaded onto said lead screw, said nut being attached to said rib cage engagement assembly; and
   iv) an operating device for rotating said screw.

\* \* \* \* \*